United States Patent
Cox et al.

(10) Patent No.: US 7,211,393 B2
(45) Date of Patent: May 1, 2007

(54) METHOD TO PROTECT DNA ENDS

(75) Inventors: Michael M. Cox, Oregon, WI (US); Dennis R. Harris, Madison, WI (US); Sergei V. Saveliev, Madison, WI (US); John R. Battista, Baton Rouge, LA (US); Edmond Jolivet, Limours-en-Hurepoix (FR); Masashi Tanaka, Kagoshima (JP); Julie M. Eggington, Madison, WI (US)

(73) Assignees: Board of Supervisors of Louisiana State University and Agricultural and Mechanical College, Baton Rouge, LA (US); Wisconsin Alumni Research Foundation, Madison, WI (US)

( * ) Notice: Subject to any disclaimer, the term of this patent is extended or adjusted under 35 U.S.C. 154(b) by 0 days.

(21) Appl. No.: 11/123,701

(22) Filed: May 6, 2005

(65) Prior Publication Data

US 2006/0024698 A1   Feb. 2, 2006

Related U.S. Application Data

(60) Provisional application No. 60/569,198, filed on May 7, 2004.

(51) Int. Cl.
*C12Q 1/68* (2006.01)
*C07K 14/00* (2006.01)

(52) U.S. Cl. .......................................... 435/6; 530/350
(58) Field of Classification Search ..................... None
See application file for complete search history.

(56) References Cited

U.S. PATENT DOCUMENTS

2003/0228616 A1*  12/2003  Arezi et al. ................... 435/6

OTHER PUBLICATIONS

Koboyashi et al. ("Effect of the space environment on the induction of DNA-repair related proteins and recovery from radiation damage" Adv Space Res. 2000;25(10):2103-6).*
Miller et al. ("Genetic variability in susceptibility and response to toxicants" Toxicol Lett 2001 Mar. 31;120(1-3):269-80).*
Bernstein D, et al., "Crystal structure of the *Deinococcus radiodurans* single-stranded DNA-binding protein suggests a mechanism for coping with DNA damage," Proc. Natl. Acad. Sci. USA 101:8575-8580 (2004).
Clark A, "rec genes and homologous recombination proteins in *Escherichia coli*," Biochimie. 73:523-532 (1991).
Harris D, et al., "Preserving genome integrity: the DdrA protein of *Deinococcus radiodurans* R1," PLoS Biol. 2:e304 (2004).
Tanaka M, et al., "Analysis of *Deinococcus radiodurans's* transcriptional response to ionzing radiation and desiccation reveals novel proteins that contribute to extreme radioresistance," Genetics 168:21-33 (2004).

* cited by examiner

*Primary Examiner*—Jeffrey Fredman
*Assistant Examiner*—Christopher M. Babic
(74) *Attorney, Agent, or Firm*—Quarles & Brady LLP

(57) ABSTRACT

A method of protecting the 3' end of a DNA molecule from nuclease damage is disclosed. In one embodiment, the method comprises the step of exposing the DNA molecule to a preparation of DdrA protein.

15 Claims, 10 Drawing Sheets

SEQUENCE LISTING

```
<160> NUMBER OF SEQ ID NOS: 18

<210> SEQ ID NO 1
<211> LENGTH: 727
<212> TYPE: DNA
<213> ORGANISM: Deinococcus radiodurans
<220> FEATURE:
<221> NAME/KEY: CDS
<222> LOCATION: (51)..(674)

<400> SEQUENCE: 1
ctggcgtttt atgtcttgac cgtaatgtta ttctgttcta aactaaatgc atg aag          56
                                                         Met Lys
                                                           1 ctg agc gat gtc cag aaa cga ctg caa gcc ccg ttt ccc gct cat acc       104
Leu Ser Asp Val Gln Lys Arg Leu Gln Ala Pro Phe Pro Ala His Thr
        5                   10                  15 gtg agc tgg aag ccc gcc gct ttc aac gcc gag cgc acc cgc gcc ctg       152
Val Ser Trp Lys Pro Ala Ala Phe Asn Ala Glu Arg Thr Arg Ala Leu
    20                  25                  30 ctg ctg gct cac gtg gac gcc cgc gcg gtg cag gac cga ctc gac gcc       200
Leu Leu Ala His Val Asp Ala Arg Ala Val Gln Asp Arg Leu Asp Ala
35                  40                  45                  50
```

-continued

| | | |
|---|---|---|
| gtt tgc ccc gac gac tgg agc ttt gag atg gaa gtg gtg tcc ggt gcg<br>Val Cys Pro Asp Asp Trp Ser Phe Glu Met Glu Val Val Ser Gly Ala<br>55                  60                  65 | | 248 |
| gaa gtg ccc acc gtc aag ggc cgc ctg acc gtg ctc ggc gtg acc cgc<br>Glu Val Pro Thr Val Lys Gly Arg Leu Thr Val Leu Gly Val Thr Arg<br>  70                  75                  80 | | 296 |
| gag gat atc ggc gag gcg cct gag ggc agc atg gcg gcg tac aag gcg<br>Glu Asp Ile Gly Glu Ala Pro Glu Gly Ser Met Ala Ala Tyr Lys Ala<br>85                  90                  95 | | 344 |
| gcg gcg agc gac gcc atg aag cgc tgc gcg gtg cag ttc ggc atc ggg<br>Ala Ala Ser Asp Ala Met Lys Arg Cys Ala Val Gln Phe Gly Ile Gly<br>    100                 105                 110 | | 392 |
| cgt tac ctc tac gac ctg ccc aag cag tgg gcc gac tgg gac gat gcc<br>Arg Tyr Leu Tyr Asp Leu Pro Lys Gln Trp Ala Asp Trp Asp Asp Ala<br>115                 120                 125                 130 | | 440 |
| cgg cgc ggc ccc aag cac ctg ccc gag ctg ccc gag tgg gca cgc ccc<br>Arg Arg Gly Pro Lys His Leu Pro Glu Leu Pro Glu Trp Ala Arg Pro<br>            135                 140                 145 | | 488 |
| gac cac gaa cgc acc ccc ggc ggc gcc cac ctg gtg cag gcg atg gag<br>Asp His Glu Arg Thr Pro Gly Gly Ala His Leu Val Gln Ala Met Glu<br>        150                 155                 160 | | 536 |
| cag ttg cgc tac gaa ctg ccc gag gac ctc gac ctg caa cgt gag gtc<br>Gln Leu Arg Tyr Glu Leu Pro Glu Asp Leu Asp Leu Gln Arg Glu Val<br>    165                 170                 175 | | 584 |
| tac aag cac ctc aag gcc gcg ctc ggc agc att cac cct gtc ccg act<br>Tyr Lys His Leu Lys Ala Ala Leu Gly Ser Ile His Pro Val Pro Thr<br>180                 185                 190 | | 632 |
| ggt ccc gtg ccg acc aac ccg gtg cag ggc ggg agg gcc gca<br>Gly Pro Val Pro Thr Asn Pro Val Gln Gly Gly Arg Ala Ala<br>195                 200                 205 | | 674 |
| tgacccgcag cctgacctct gccgagctgc gcggggggggc ggctccctcc gtc | | 727 |

<210> SEQ ID NO 2
<211> LENGTH: 208
<212> TYPE: PRT
<213> ORGANISM: Deinococcus radiodurans

<400> SEQUENCE: 2

Met Lys Leu Ser Asp Val Gln Lys Arg Leu Gln Ala Pro Phe Pro Ala
1               5                   10                  15

His Thr Val Ser Trp Lys Pro Ala Ala Phe Asn Ala Glu Arg Thr Arg
            20                  25                  30

Ala Leu Leu Leu Ala His Val Asp Ala Arg Ala Val Gln Asp Arg Leu
        35                  40                  45

Asp Ala Val Cys Pro Asp Asp Trp Ser Phe Glu Met Glu Val Val Ser
    50                  55                  60

Gly Ala Glu Val Pro Thr Val Lys Gly Arg Leu Thr Val Leu Gly Val
65                  70                  75                  80

Thr Arg Glu Asp Ile Gly Glu Ala Pro Glu Gly Ser Met Ala Ala Tyr
                85                  90                  95

Lys Ala Ala Ala Ser Asp Ala Met Lys Arg Cys Ala Val Gln Phe Gly
            100                 105                 110

Ile Gly Arg Tyr Leu Tyr Asp Leu Pro Lys Gln Trp Ala Asp Trp Asp
        115                 120                 125

Asp Ala Arg Arg Gly Pro Lys His Leu Pro Glu Leu Pro Glu Trp Ala
    130                 135                 140

Arg Pro Asp His Glu Arg Thr Pro Gly Gly Ala His Leu Val Gln Ala
145                 150                 155                 160

```
Met Glu Gln Leu Arg Tyr Glu Leu Pro Glu Asp Leu Asp Leu Gln Arg
                165                 170                 175

Glu Val Tyr Lys His Leu Lys Ala Ala Leu Gly Ser Ile His Pro Val
            180                 185                 190

Pro Thr Gly Pro Val Pro Thr Asn Pro Val Gln Gly Gly Arg Ala Ala
            195                 200                 205

<210> SEQ ID NO 3
<211> LENGTH: 6
<212> TYPE: PRT
<213> ORGANISM: Deinococcus radiodurans

<400> SEQUENCE: 3

Met Lys Leu Ser Asp Val
1               5

<210> SEQ ID NO 4
<211> LENGTH: 29
<212> TYPE: DNA
<213> ORGANISM: Artificial
<220> FEATURE:
<223> OTHER INFORMATION: Synthetic oligonucleotide

<400> SEQUENCE: 4
ggtgcaggac cgactcgacg ccgtttgcc                                        29

<210> SEQ ID NO 5
<211> LENGTH: 29
<212> TYPE: DNA
<213> ORGANISM: Artificial
<220> FEATURE:
<223> OTHER INFORMATION: Synthetic oligonucleotide

<400> SEQUENCE: 5
cctcgcgggt cacgccgagc acggtcagg                                        29

<210> SEQ ID NO 6
<211> LENGTH: 30
<212> TYPE: DNA
<213> ORGANISM: Artificial
<220> FEATURE:
<223> OTHER INFORMATION: Synthetic oligonucleotide

<400> SEQUENCE: 6
gtcagcaccg gcagcctcag ccttgacctc                                       30

<210> SEQ ID NO 7
<211> LENGTH: 26
<212> TYPE: DNA
<213> ORGANISM: Artificial
<220> FEATURE:
<223> OTHER INFORMATION: Synthetic oligonucleotide

<400> SEQUENCE: 7
gatggcgagg gccagggtgg tcttgc                                           26

<210> SEQ ID NO 8
<211> LENGTH: 29
<212> TYPE: DNA
<213> ORGANISM: Artificial
<220> FEATURE:
<223> OTHER INFORMATION: Synthetic oligonucleotide

<400> SEQUENCE: 8
```

```
cttcaccagc cgcgaagggg cctccaagc                                     29

<210> SEQ ID NO 9
<211> LENGTH: 27
<212> TYPE: DNA
<213> ORGANISM: Artificial
<220> FEATURE:
<223> OTHER INFORMATION: Synthetic oligonucleotide

<400> SEQUENCE: 9
gcccagcacg atggagaagt cctcgcc                                       27

<210> SEQ ID NO 10
<211> LENGTH: 51
<212> TYPE: DNA
<213> ORGANISM: Artificial
<220> FEATURE:
<223> OTHER INFORMATION: Synthetic oligonucleotide

<400> SEQUENCE: 10
ttaacgaccg tcgacctgca ggtcgacggt cgttaacgtc tctcagattg t            51

<210> SEQ ID NO 11
<211> LENGTH: 51
<212> TYPE: DNA
<213> ORGANISM: Artificial
<220> FEATURE:
<223> OTHER INFORMATION: Synthetic oligonucleotide

<400> SEQUENCE: 11
cgtctctcag attgtttaac gaccgtcgac ctgcaggtcg acggtcgtta a            51

<210> SEQ ID NO 12
<211> LENGTH: 51
<212> TYPE: DNA
<213> ORGANISM: Artificial
<220> FEATURE:
<223> OTHER INFORMATION: Synthetic oligonucleotide

<400> SEQUENCE: 12
ggtctttcaa attgtttaag gaagaaacta atgctagcca cggtccgagc c            51

<210> SEQ ID NO 13
<211> LENGTH: 51
<212> TYPE: DNA
<213> ORGANISM: Artificial
<220> FEATURE:
<223> OTHER INFORMATION: Synthetic oligonucleotide

<400> SEQUENCE: 13
ggctcggacc gtggctagca ttagtttctt ccttaaacaa tttgaaagac c            51

<210> SEQ ID NO 14
<211> LENGTH: 30
<212> TYPE: DNA
<213> ORGANISM: Artificial
<220> FEATURE:
<223> OTHER INFORMATION: Synthetic oligonucleotide

<400> SEQUENCE: 14
gtgcgctccg agctcagcta ccgcgaggcc                                    30

<210> SEQ ID NO 15
<211> LENGTH: 50
<212> TYPE: DNA
<213> ORGANISM: Artificial
```

-continued

```
<220> FEATURE:
<223> OTHER INFORMATION: Synthetic oligonucleotide

<400> SEQUENCE: 15
ggcctcgcgg tagctgagct cggagcgcac gattcgcact gctgatgttc          50

<210> SEQ ID NO 16
<211> LENGTH: 37
<212> TYPE: DNA
<213> ORGANISM: Artificial
<220> FEATURE:
<223> OTHER INFORMATION: Synthetic oligonucleotide

<400> SEQUENCE: 16
ctagcattag tttcttcctt aaacaatttg aaagacc                        37

<210> SEQ ID NO 17
<211> LENGTH: 18
<212> TYPE: DNA
<213> ORGANISM: Artificial
<220> FEATURE:
<223> OTHER INFORMATION: Synthetic oligonucleotide

<400> SEQUENCE: 17
aagcacaatt acccacgc                                             18

<210> SEQ ID NO 18
<211> LENGTH: 30
<212> TYPE: DNA
<213> ORGANISM: Artificial
<220> FEATURE:
<223> OTHER INFORMATION: Synthetic oligonucleotide

<400> SEQUENCE: 18
gcgtgggtaa ttgtgcttca atggactgac                                30
```

METHOD TO PROTECT DNA ENDS

CROSS-REFERENCE TO RELATED APPLICATION

This application claims priority to U.S. provisional Ser. No. 60/569,198, filed May 7, 2004, incorporated by reference herein.

STATEMENT REGARDING FEDERALLY SPONSORED RESEARCH OR DEVELOPMENT

This invention is made with United States government support awarded by the following agencies: NIH GM052725 and GM 067085. The United States has certain rights in this invention.

BACKGROUND OF THE INVENTION

*Deinococcus radiodurans* is a non-sporeforming bacterium notable for its capacity to tolerate exposure to ionizing radiation (Battista and Rainey, Phylum BIV. "*Deinococcus*-Thermus" Family 1. Deinococcaceae Brooks and Murray 1981, 356,$^{vp}$ emend. Rainey, Nobre, Schumann, Stackebrandt and da Costa 1997, 513. In: Boone D R, Castenholz R W, editors, Bergey's Manual of Systematic Bacteriology, 2nd ed. New York: Springer, pp. 395–414, 2001). The $D_{37}$ dose for *D. radiodurans* R1 is approximately 6500Gy, at least 200-fold higher than the $D_{37}$ dose of *E. coli* cultures irradiated under the same conditions. The energy deposited by 6500Gy γ radiation should introduce thousands of DNA lesions including hundreds of double strand breaks (Smith, et al., Molecular biology of radiation resistant bacteria, In: Herbert R A, Sharp R J, editors, Molecular biology and biotechnology of extremophiles, New York: Chapman & Hall, pp. 258–280, 1992). The mechanisms responsible for this species' resilience are poorly described and recent analyses of DNA damage-induced changes in the proteome (Lipton, et al., *Proc. Natl. Acad. Sci. USA* 99(17):11049–11054, 2002) and transcriptome (Liu, et al., *Proc. Natl. Acad. Sci. USA* 100(7):4191–4196, 2003) of *D. radiodurans* cultures have done little to improve our understanding of *D. radiodurans*' radioresistance (Edwards and Battista, *Trends Biotechnol.* 21 (9):381–382, 2003; Narumi, *Trends Microbiol.* 11 (9):422–425, 2003).

For most species, the intracellular generation of strand breaks has lethal consequences; exposed free ends serving as substrates for intracellular exonucleases that degrade the genome. However, in *D. radiodurans* the presence of strand breaks does not result in a catastrophic loss of genetic information (Dean, et al., *Nature* 209(18):49–52, 1966; Lett, et al., *Proc. R. Soc. Lond. B. Biol. Sci.* 167(7):184–201, 1967; Vukovic-Nagy, et al., *Int. J. Radiat. Biol. Relat. Stud. Phys. Chem. Med.* 25(4):329–337, 1974). Instead this species appears to have the ability to control DNA degradation post-irradiation by synthesizing proteins that prevent extensive digestion of the genome, and it has been suggested that the DNA degradation observed in this species is an integral part of the process of DNA repair, generating single-stranded DNA that promotes homologous recombination and restitution of the damaged genome (Battista, et al., Phylum BIV. "*Deinococcus*-Thermus" Family 1. Deinococcaceae Brooks and Murray 1981, 356,$^{vp}$ emend. Rainey, Nobre, Schumann, Stackebrandt and da Costa 1997, 513. In: Boone D R, Castenholz R W, editors. Bergey's Manual of Systematic Bacteriology. 2nd ed. New York: Springer, pp. 395–414, 1999).

When *D. radiodurans* is exposed to a high dose of ionizing radiation, a number of genes are induced that lack readily identifiable homologues among known prokaryotic proteins (Liu, et al., supra, 2003; Tanaka, et al., *Genetics* 168:210–233, 2003). Among these is the gene designated DR0423 (Q9RX92). This locus is one of the most highly induced genes in *Deinococcus* following γ-irradiation, expression increasing 20–30 fold relative to an untreated control. Although originally annotated as a "hypothetical" protein (White, et al., *Science* 286(5444):1571–1577, 1999), a more detailed analysis (Iyer, et al., *BMC Genomics* 3(1):8, 2002) has identified an evolutionary relationship between DR0423p and the important eukaryotic recombination protein Rad52 (P06778). Rad52 is part of a larger family of proteins exhibiting structural similarity but little sequence homology, including the prokaryotic Redβ (P03698), RecT (NC 000913.1), and Erf ($PO_{4892}$) proteins (Passy, et al., *Proc. Natl. Acad. Sci. USA* 96(8):4279–4284, 1999; Iyer, et al., supra, 2002).

BRIEF SUMMARY OF THE INVENTION

In one embodiment, the present invention is a method of protecting the 3' end of a DNA molecule from nuclease damage comprising the step of exposing the DNA molecule to an amount of a preparation of DdrA protein effective to decrease nuclease damage. Preferably, the DdrA protein is incubated with at least a first and a second linear duplex DNA each with a 3'-ending strand and a 5'-ending strand, wherein the first linear duplex DNAs comprises an end that is complementary to an end of the second linear duplex DNA. One could expose the first and second DNA molecule to a exonuclease, wherein the DdrA protein protects the 3' ending strands while allowing the 5' ending strands to be degraded, thereby producing single-stranded extensions with 3' ends on both first and second DNAs. Preferably, the method comprises the steps of annealing the single stranded extensions of the first and second DNAs, thereby producing a joined first and second DNA. One would then process the joined DNA with a nuclease, a DNA polymerase, and a DNA ligase to make the joined DNA contiguous.

The present invention is also a preparation of DdrA protein, and a polynucleotide encoding the protein.

Other embodiments, features and advantages of the present invention will become apparent on review of the specification, claims and drawings.

BRIEF DESCRIPTION OF THE SEVERAL VIEWS OF THE DRAWINGS

(FIG. 1A) Verification of DR0423 and recA gene deletions by PCR analysis. Purified PCR fragments were amplified from the genomic DNA of strains R1, TNK104, TNK106, and TNK110 using primers that flank the coding sequences for DR0423 (ddrA) and DR2340 (recA). Products were separated on a 0.8% agarose gel to establish whether the fragment size corresponded to the gene replacement cassette. The left panel depicts the replacement of ddrA in TNK104 and TNK110. The right panel depicts the replacement of recA in TNK106 and TNK110. Expected sizes of the wild type and mutant sequences are given in the figure above each image of the agarose gel. (FIG. 1B) Verification of the DR0423 (ddrA) gene deletion by restriction analysis of purified PCR products. Purified PCR fragments were ampli fied from the genomic DNA of strains R1, TNK104, and TNK110 using primers that flank the coding sequences for DR0423 (ddrA). Products were restricted with EcoR1 (left panel) and EcoRV (right panel) to verify their identity. Products were separated on a 0.8% agarose gel to establish whether the restriction fragment corresponded with the expected sizes as illustrated in the figure above each image of the agarose gel. (FIG. 1C Verification of the DR2340 (recA) gene deletion by restriction analysis of purified PCR products. Purified PCR fragments were amplified from the genomic DNA of strains R1, TNK106, and TNK110 using primers that flank the coding sequences for DR2340 (recA). Products were restricted with PvuII left panel) and BglII (right panel) to verify their identity. Products were separated on a 0.8% agarose gel to establish whether the restriction fragment corresponded with expected sizes as illustrated in the figure above each gel.

(FIG. 2A) Representative survival curves for *D. radiodurans* strain TNK104 ΔddrA (squares) and *D. radiodurans* R1 (circles) following exposure to γ radiation. Survival of strains Values are the mean±standard deviation of triplicate experiments. n=9. (FIG. 2B) Representative survival curves for *D. radiodurans* strain TNK104 ΔddrA (squares) and *D. radiodurans* R1 (circles) following exposure to mitomycin C. Values are the mean±standard deviation of three independent experiments. n=9.

(FIG. 4A) Pulsed-field gel electrophoresis analyses of *D. radiodurans* strain RI (wild type) recovery over a 120 hour time course in 10 mM MgSO$_4$ following 5000 Gy γ radiation. (FIG. 4B) Pulsed-field gel electrophoresis analyses of *D. radiodurans* strain TNK104 (ΔddrA) recovery following 5000 Gy γ radiation.

(FIG. 5A) Survival of *D. radiodurans* R1 and TNK104 cultures held in 10 mM MgSO$_4$ for 120 hour following exposure to 5000 Gy γ radiation. Samples were obtained at 24 hour intervals. All values are the mean±standard deviation of three independent experiments. n=9 (FIG. 5B) Genomic DNA loss following irradiation at 5,000 Gy.

(FIG. 7A) Single-strand oligonucleotides (51 nucleotides in length), labelled on the 5' end. (FIG. 7B) 5' end-labeled duplex DNA fragments (51 bp). (FIG. 7C) 5'-end-labelled oligonucleotide, with a self-complementary sequence leading to the formation of an 18 bp hairpin and a 15 nucleotide 5' single strand extension. (FIG. 7D) 3' end-labelled oligonucleotide, with a self-complementary sequence leading to the formation of an 18 bp hairpin and a 16 nucleotide 3' single strand extension. The sequences of the single strand extensions in the oligos used in sets C and D are matched, except that an extra adenosine residue has been added to the oligo used in set D during the labelling process. Note that in set B, only the lower substrate band (unannealed oligonucleotides) is bound by DdrA, and the migration of the resulting complexes is identical to that shown in set A.

(FIG. 8A) This set of reactions uses the labelled duplex DNA illustrated. The oligos annealed to form this DNA are 51 and 37 nucleotides in length, and pair so as to leave a 14 nucleotide 3' extension. The shorter DNA is 5' end-labelled. The first lane contains unreacted DNA, showing both the annealed duplex and the unannealed ssDNA. The second lane shows the DNA after treatment with 3 units of exonuclease I for 7 minutes in a 15 ml reaction mixture. Note that the duplex DNA in the upper band has been shortened by removal of the single strand extension. In lanes 3 and 4, the DdrA protein (4 μM) has been incubated with the DNA, without and with the 3 units of exonuclease I respectively. The bound DNA is bound by DdrA and shifted to the top of the gel. The reactions shown in lanes 5 and 6 are identical to those in lanes 3 and 4, but with added SDS and proteinase K added to disrupt the DdrA-DNA complexes and reveal that the DNA has been minimally affected by Exonuclease I. The final lane shows another reaction of the DNA with 3 units of exonuclease 1, in the presence of 4 μM BSA. Exonuclease I degrades single-stranded DNA in the 3' to 5' direction. (FIG. 8B) The protein bound to the duplex DNA is DdrA. The reaction of panel A, lane 3, was scaled up and the protein-DNA complex excised from the gel as described in Methods. The protein in this complex was subjected to electrophoresis on an SDS-polyacrylamide gel shown here (lane 3). The control lanes contained pre-stained protein standards (lane 1) and purified DdrA protein (lane 2). The gel extracted protein co-migrated with DdrA.

DESCRIPTION OF THE PRESENT INVENTION

The bacterium *Deinococcus radiodurans* can withstand extraordinary levels of ionizing radiation, reflecting an equally extraordinary capacity for DNA repair. The hypothetical gene product DR0423 has been implicated in the recovery of this organism from DNA damage, indicating that this protein is a novel component of the *D. radiodurans* DNA repair system. DR0423 is a homologue of the eukaryotic Rad52 protein.

The examples below show that following exposure to ionizing radiation, DR0423 expression is induced relative to an untreated control, and strains carrying a deletion of the DR0423 gene exhibit increased sensitivity to ionizing radiation. When recovering from ionizing radiation-induced DNA damage in the absence of nutrients, wild type *D. radiodurans* reassembles its genome while the mutant lacking DR0423 function does not.

Figure 10:
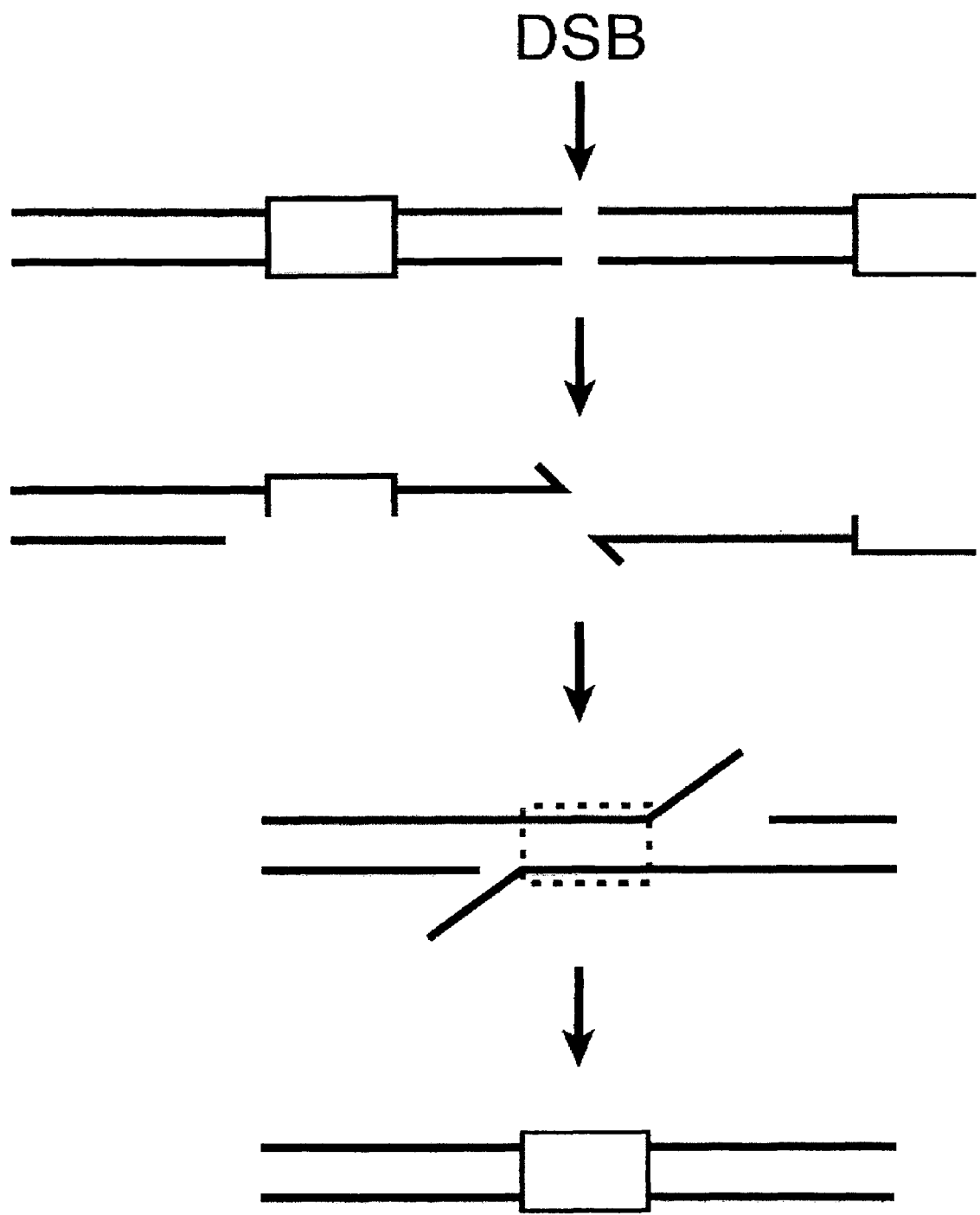
FIG. 10 is a diagram of one embodiment of the present invention.

We have found that the purified DR0423 protein binds to single-stranded DNA in vitro with an apparent affinity for 3' ends and protects those ends from nuclease degradation. We propose that DR0423 is part of a DNA end-protection system that helps to preserve genome integrity following exposure to ionizing radiation. We designate the DR0423 protein DdrA (DNA damage response protein A). The DNA and protein sequence of DdrA are disclosed at SEQ ID No. 1 and 2. FIG. 10 is a general diagram of one embodiment of the present invention.

In one embodiment of the present invention, the purified DdrA protein can be used by itself, and in combination with other factors, to specifically block DNA 3' ends in protocols requiring the generation of single-strand 3' extensions on duplex DNA. The protein can also be used in protocols designed to introduce engineered DNA at site-specific genomic locations in a wide range of cells and to join together large fragments of DNA. These embodiments of the present invention are discussed in more detail below.

By "DdrA protein" we mean that minor or conservative amino acid substitutions may be introduced to the protein and still result in a DdrA protein with equivalent functional activity. Specifically, we mean to define functional activity in terms of single-stranded DNA binding with affinity of 3' ends and protection of those ends from nuclease degradation. One may evaluate equivalent functional activity by reference to the Examples and the DNA binding assays disclosed below.

Harris, et al., *PLOS Biology* 2(110)e304, October 2004 (incorporated herein by reference) and the examples below describe experiments showing the evidence for a DNA end-protection system in *D. radiodurans* and the characterization of the DR0423 protein as a component of that system. Bernstein, et al., *Proc. Natl. Acad. Sci.* 101(23): 8575–8580, 2004, incorporated herein by reference, describes the crystal structure of *Deinococcus radiodurans* SSB protein (DrSSB). Tanaka, et al., *Genetics* 168:210–233 (September, 2004), incorporated herein by reference, describes the analysis of *D. radiodurans* transcriptional response to ionizing radiation.

As disclosed above, we envision that one would wish to use the DdrA protein in various methods to protect DNA ends in cloning methods. For example, one may wish to add the DdrA protein to a double-stranded or single-stranded preparation of DNA that may be exposed to exonuclease activity. The presence of the DdrA protein will ensure that the 3'-end is protected from nuclease degradation.

In another preferable method of the present invention, one could use the DdrA protein to join DNA strands. For example, one would obtain the DdrA protein through conventional molecular biological methods and expose the protein to specific DNA molecules in the following manner: DdrA protein could be incubated with different linear duplex DNAs that included overlapping sequences at their ends (for example, see FIG. 10). If the DdrA protein were added to a reaction containing these DNAs and exonucleases, the DdrA protein would protect the 3'-ending strands while allowing the 5'-ending strands to be degraded. This would produce single-stranded extensions with 3' ends on both DNAs. The complementary sequences on the DNAs could then be annealed, effectively joining the two DNAs. The DNAs could be further processed with commercially available nucleases, a DNA polymerase and DNA ligase to make the two joined DNAs contiguous. The method could be used to join long (1 kilobase pair or longer) DNAs and could be employed to reconstruct large chromosome-sized DNAs (100 kilobase pairs or larger) from complex mixtures of large DNA fragments derived from the chromosomes.

In such protocols, the DdrA protein would be used at concentrations ranging from 1–5 nanomolar to 100 micromolar. The DNA fragments or molecules would be typically used at 0.1–100 nanomolar concentrations (in total molecules). Preferably, one would wish to use concentrations of DdrA of 1–10 micromolar. Preferably, the DNA is protected for at least 30 minutes. Typically, a reaction condition of pH 7–7.5 and 25–36° C. is preferred. Other preferred conditions are described below in the Examples.

Additionally, one may wish to use the method of the present invention as part of larger system involving other protective molecules. For example, we have demonstrated that the *D. radiodurans* SSB protein is also involved in DNA end protection and one might wish to use two proteins synergistically in the following manner: DrSSB could be used as an additional reagent to facilitate the reactions of FIG. 10. DrSSB is involved in almost all reactions involving DNA, and plays an important role in the recovery of *Deinococcus radiodurans* from high levels of DNA damage (See Saveliev, et al., supra). In crude extracts, the DrSSB protein helps to protect 3'-ending DNA strands while allowing 5'-ending strands to be degraded. This activity should facilitate the types of DNA engineering reactions envisioned in FIG. 10. Eggington, et al. (*BMC Microbiology* 4:2, January, 2004) describes the purification of DrSSB, as well as the correction of the gene sequence.

The present invention is also a preparation of the DdrA protein and an isolated polynucleotide encoding these proteins. By "preparation" we mean any version of the DdrA protein that is purified relative to its naturally occurring embodiment in *D. radiodurans*. A crude preparation of *D. radiodurans* in which the DdrA protein is enhanced is a "preparation of the DdrA protein." Preferably, for use in the cloning and molecular biology protocols described above, one would wish to use the DdrA protein in a highly purified form. Most preferably, this protein would be substantially pure. One would obtain the isolated polynucleotide encoding the protein through standard molecular biological methods using the information described in the Exhibits.

SEQ ID NOs:1 and 2 are nucleic acid and protein sequences for DdrA. The gene encoding DrSSB protein was incorrectly sequenced and annotated as two separate genes listed as DR0099 and DR0100 in White, et al. *Science* 286:1571–1577, 1999. The sequence has recently been corrected (The single-stranded DNA-binding protein of *Deinococcus radiodurans*, Eggington, et al., *BMC Microbiology* 4:2, 2004), demonstrating that the ssb gene consists of sequences making up both DR0099, DR0100, and intervening sequences combined into one single gene. The DR0099 and DR0100 genes have accession number NC_001263. The corrected ssb sequence, reported here, has accession number AY293617.

EXAMPLES

In this report, we provide evidence for a DNA end-protection system in *D. radiodurans*, and characterize the DR0423 protein as a component of that system. Our studies suggest that DNA end-protection might be particularly important to this species in the context of long-term survival during desiccation and recovery in a nutrient-poor environment. The majority of the work in this Example may be found in Harris, et al., supra.

Results

Transcripts Corresponding to the Coding Sequence Designated DR0423 Increase in Response to Sub-Lethal Doses of Ionizing Radiation During the course of microarray studies intended to establish which R1 loci respond to ionizing radiation, it was noted that transcripts of DR0423 were among the mostly highly induced (Tanaka, et al., supra, 2003). As an independent confirmation of these microarray results, the expression of this gene was monitored using quantitative real time PCR. Total RNA was isolated from exponential phase cultures of R1 immediately after and at 30 and 60 minutes following exposure to 3000Gy ionizing radiation. Changes in transcript abundance for the recA (DR2340) (P42443), gap (DR1343) (Q9RUP1) and DR0423 genes were determined as previously described (Earl, et al., *J. Bacteriol.* 184(22): 6216–6224, 2002a). The results of these analyses are listed in Table 1. Consistent with previous results, levels of recA transcript increased post-irradiation (Narumi, et al., *J. Bacteriol.* 183(23):6951–6956, 2001; Bonacossa de Almeida, et al., *Mol. Genet. Genomics* 268(1):28–41, 2002; Satoh, et al., *J. Biochem.* (Tokyo) 131(1):121–129, 2002), whereas gap induction remained unchanged (Earl, et al., *J. Bacteriol.* 184(22):6216–6224, 2002a). The gap gene encodes glyceraldehyde 3-phosphate dehydrogenase, and does not respond to DNA damage. Within one half hour post-irradiation, levels of DR0423 transcript increased between 20–30 fold, suggesting that DR0423p may be a previously unrecognized component of the cell's defense against ionizing radiation-induced damage.

Figure 1:
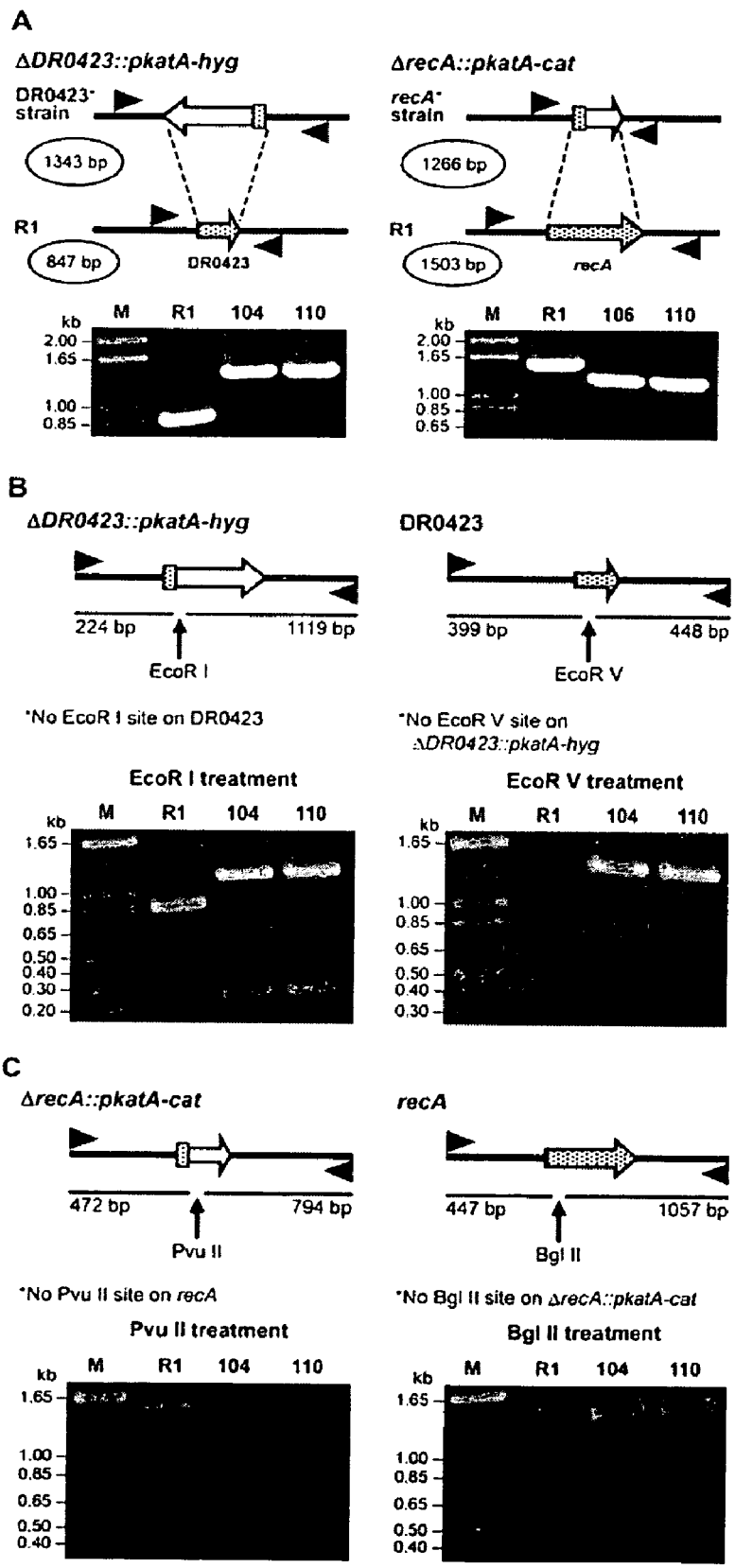
FIG. 1 illustrates verification of gene deletions.

Deletion of DR0423 Sensitizes *D. radiodurans* R1 to Ionizing Radiation and Mitomycin C The DR0423 gene was inactivated by deletion in *D. radiodurans* R1, as described elsewhere (Tanaka, et al., supra, 2003; Funayama, et al., *Mutat. Res.* 435(2):151–161, 1999), and the resulting strain designated TNK104. Confirmation of the gene deletion is provided in FIG. 1. Deletion of DR0423 does not alter the growth rate of the culture (~1.5 hour doubling time), or decrease the efficiency of natural transformation (~5×10$^{-5}$ rifampicin resistant transformants per colony forming unit) relative to R1, indicating that DR0423p is not essential for the processes of DNA replication or homologous recombination. To establish whether DR0423p was necessary for DNA damage tolerance, TNK104 was evaluated for its ability to survive ionizing radiation and mitomycin C. Aliquots of exponential phase cultures were exposed to these DNA damaging agents. TNK104 exhibits increased sensitivity to both agents relative to the wild-type R1 strain (FIG. 2), but cultures only displayed significant IR sensitivity at doses in excess of 5000Gy. Since expression of DR0423 increases in response to ionizing radiation and its gene product contributes to the DNA damage resistance of this species, we have chosen to designate this gene as ddrA (DNA damage response).

Figure 3:
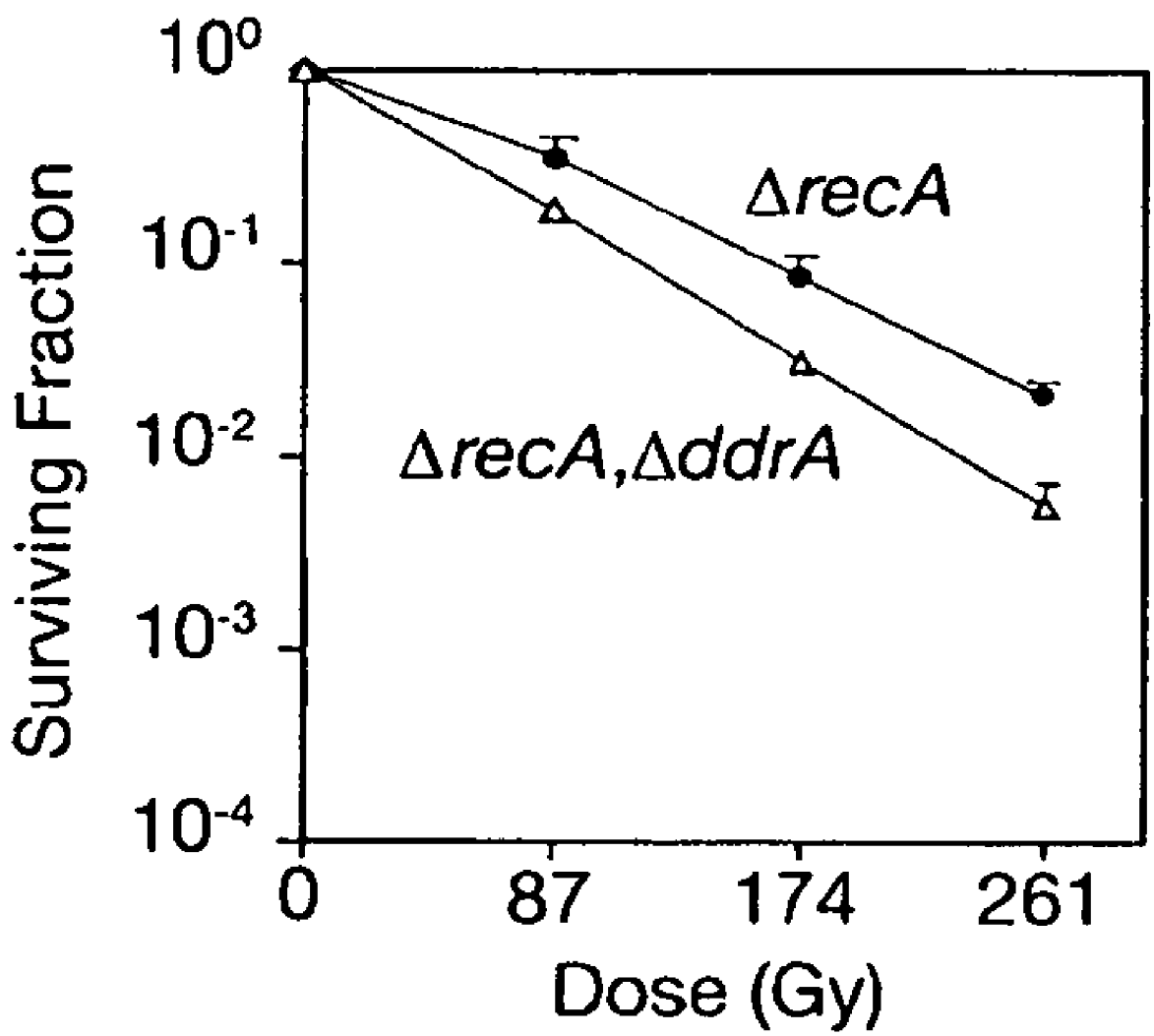
FIG. 3 graphs DdrA functions in a RecA-independent DNA repair process. Representative survival curves for *D. radiodurans* strains TNK106 ΔrecA (closed circles) and TNK110 ΔddrA ΔrecA (open triangles) following exposure to lower levels of γ radiation. All values are the mean±standard deviation of three independent experiments. n=9.

A ddrA recA Double Mutant is More Sensitive to Ionizing Radiation than Either Single Mutant The recA gene (DR2340) was deleted from R1 and TNK104 (see FIG. 1B, C), resulting in strains TNK106 (ΔrecA) and TNK110 (ΔrecA, ΔddrA), respectively. Deinococcal strains lacking recA function are considered the most ionizing radiation sensitive strains described for this species (Moseley and Copland, *J. Bacteriol.* 121(2):422–428, 1975; Gutman, et al., *Gene* 141(1):31–37, 1994). However, as indicated in FIG. 3, TNK110 is 3–5 fold more sensitive to ionizing radiation than the ΔrecA strain, indicating that DdrA, at least in part, contributes to *D. radiodurans*' survival by a mechanism that is independent of RecA function.

Evidence that the DdrA Protein Contributes to Genome Restitution

To determine if loss of DdrA affected genome restitution and stability post-irradiation, we followed the recovery of cultures of R1 and TNK104 following a 5000Gy dose of γ radiation. Initially, exponential phase cultures were harvested and suspended in 10 mM MgSO$_4$ and irradiated. No carbon source was added. Restoration of the genome was monitored by pulsed field gel electrophoresis and aliquots retrieved from the recovering cultures were used to determine viability. Cultures were left in this medium and sampled at 24 hour intervals over a 120 hour time course.

Figure 2:
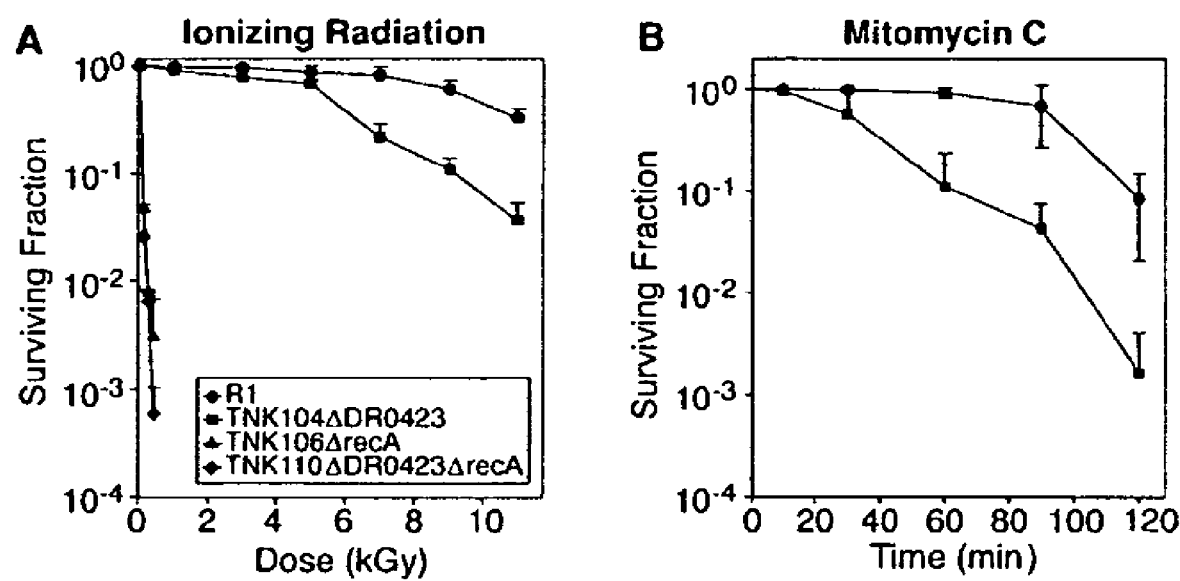
FIG. 2 graphs the DNA damage sensitivity of *Deinococcus radiodurans* cells lacking DR0423 function.
Figure 4:
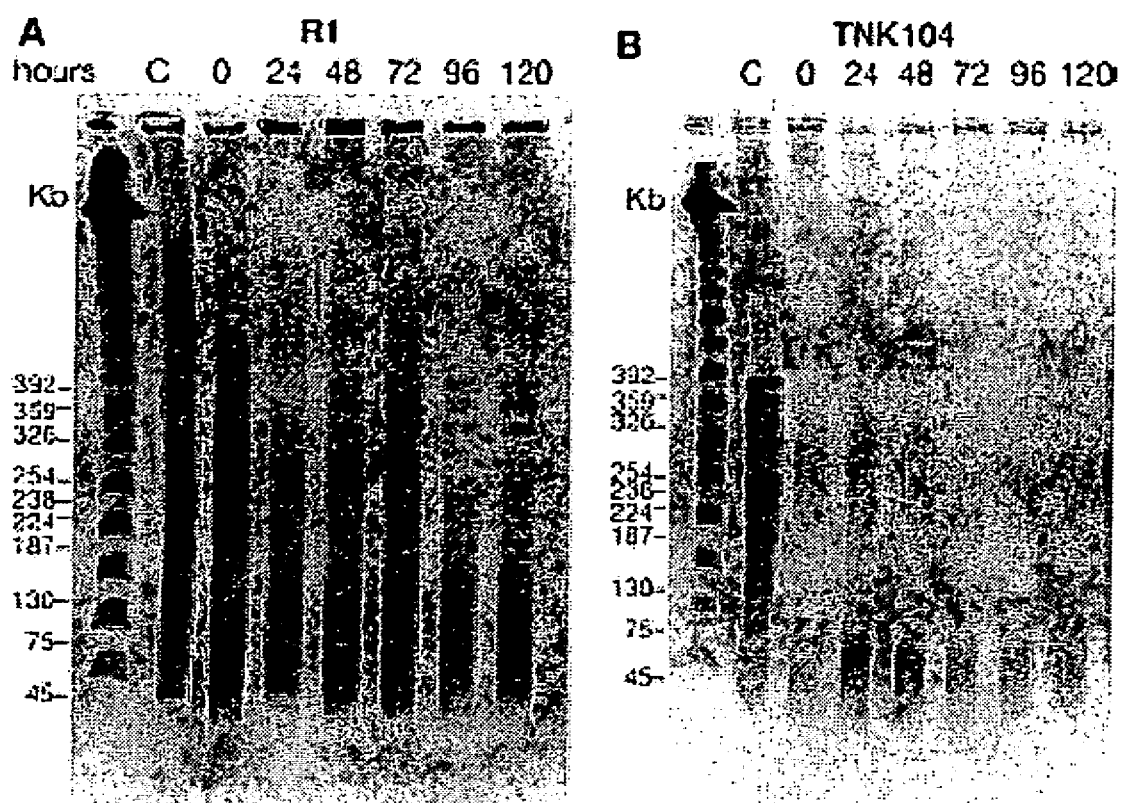
FIG. 4 illustrates genome recovery in the absence of nutrients depends on DdrA.

The gel depicted in FIG. 4 illustrates the re-assembly of the genomes of irradiated R1 cells. There are 11 NotI sites in the *Deinococcus radiodurans* genome, and when restricted most of the resulting fragments can be separated by pulsed field gel electrophoresis as seen in the lane (C) corresponding to the unirradiated control. Immediately after irradiation, the introduction of DNA double strand breaks (DSBS) results in the disappearance of the higher molecular weight NotI fragments, but the pattern of fragments is restored in 24–48 hours, indicating that R1 is repairing DSBs under these conditions, in spite of the absence of nutrients. This pattern persists throughout the rest of the time course, indicating that once re-formed the genome is stable. Despite genome restitution, R1 cultures held in MgSO$_4$ are not as proficient at recovering from ionizing radiation-induced damage as cultures that are allowed to recover in rich media (FIG. 4 and data not shown). Even if plated immediately after exposure, R1 cultures suspended in MgSO$_4$ exhibit a modest twofold reduction in viability when exposed to 5000Gy γ radiation relative to R1 cultures irradiated in rich media (FIG. 2). The longer the culture is held in MgSO$_4$ (FIG. 5) the greater the reduction in viability. After 120 hours, approximately 10% of the irradiated R1 population remains viable. In comparison, 80% of an unirradiated exponential phase population of R1 is viable when kept in 10 mM MgSO$_4$ for five days (data not shown).

Irradiated TNK104 cultures are significantly more vulnerable ionizing radiation during a prolonged incubation in MgSO$_4$ (FIG. 5A). TNK104 cultures exhibit only 0.1% survival after 120 hours, a 100-fold reduction relative to identically treated R1 cultures. Also, in sharp contrast to the R1 cultures, there is no evidence of genome reassembly in the TNK104 cells over this time course (FIG. 5A).

We also directly examined the influence of DdrA on the fate of genomic DNA (FIG. 5B) by monitoring changes in DNA content as the cultures of R1 and TNK104 recovered from exposure to 5000 Gy in MgSO$_4$. An aliquot of each unirradiated culture was isolated and total DNA concentration for 10$^6$ colony forming units (cfu) calculated. Following irradiation, the DNA content of a volume corresponding to the original 10$^6$ cfu of each culture was determined. The DNA concentration at each time point in FIG. 5B is expressed as a percentage of that present in each strain prior to irradiation. Immediately after irradiation, the genomic DNA in the R1 culture was reduced by approximately 18%, a value consistent with previous findings (Dean, et al., supra, 1966; Lett, et al., supra, 1967; Vukovic-Nagy, et al., supra, 1974) that indicate that 20–25% of the genomic DNA of *D. radiodurans* will be degraded and expelled from the cell following exposure to 5000 Gy γ radiation. In contrast, genomic DNA degradation in the strain lacking DR0423 approached 55%. Thus, the presence of DR0423 has a greater than three fold effect on the preservation of genomic DNA at early times after irradiation. In the succeeding 120 hours, the R1 genomic DNA had been reduced by a total of 31%, while the loss of genomic DNA increased to 64% in TNK104. These results suggest that DR0423 has a direct effect on the preservation of genomic DNA following extreme insults.

We also examined genome restitution in a rich medium (TGY broth). Consistent with the survival curve depicted in FIG. 2, we found that when TNK104 cells are exposed to 5000Gy their genomes reassemble with kinetics identical to those of the wild type R1 culture (Grimsley, et al., *Int. J. Radiat. Biol.* 60(4):613–626, 1991; Mattimore and Battista, *J. Bacteriol.* 178(3):633–637, 1996); the genome reforming in less than 6 hours (data not shown). Thus, DdrA appears to contribute to genome reconstruction in *D. radiodurans* following irradiation, but this role was only obvious in cultures suspended in MgSO$_4$. There could be at least two explanations for this observation. First, the action of DdrA may overlap with the activity of at least one other protein, and that while each redundant activity is functional in rich media, only DdrA is functional in cultures held in MgSO$_4$. Alternatively, the primary role of DdrA could be the passive protection of exposed 3' DNA ends at the sites of DNA strand breaks. Under conditions with limiting nutrient availability, DdrA could contribute to genome restitution simply by preventing the massive genomic degradation evident in FIG. 5B. In a rich media, active DNA repair may render DdrA-mediated DNA protection less important.

Figure 6:
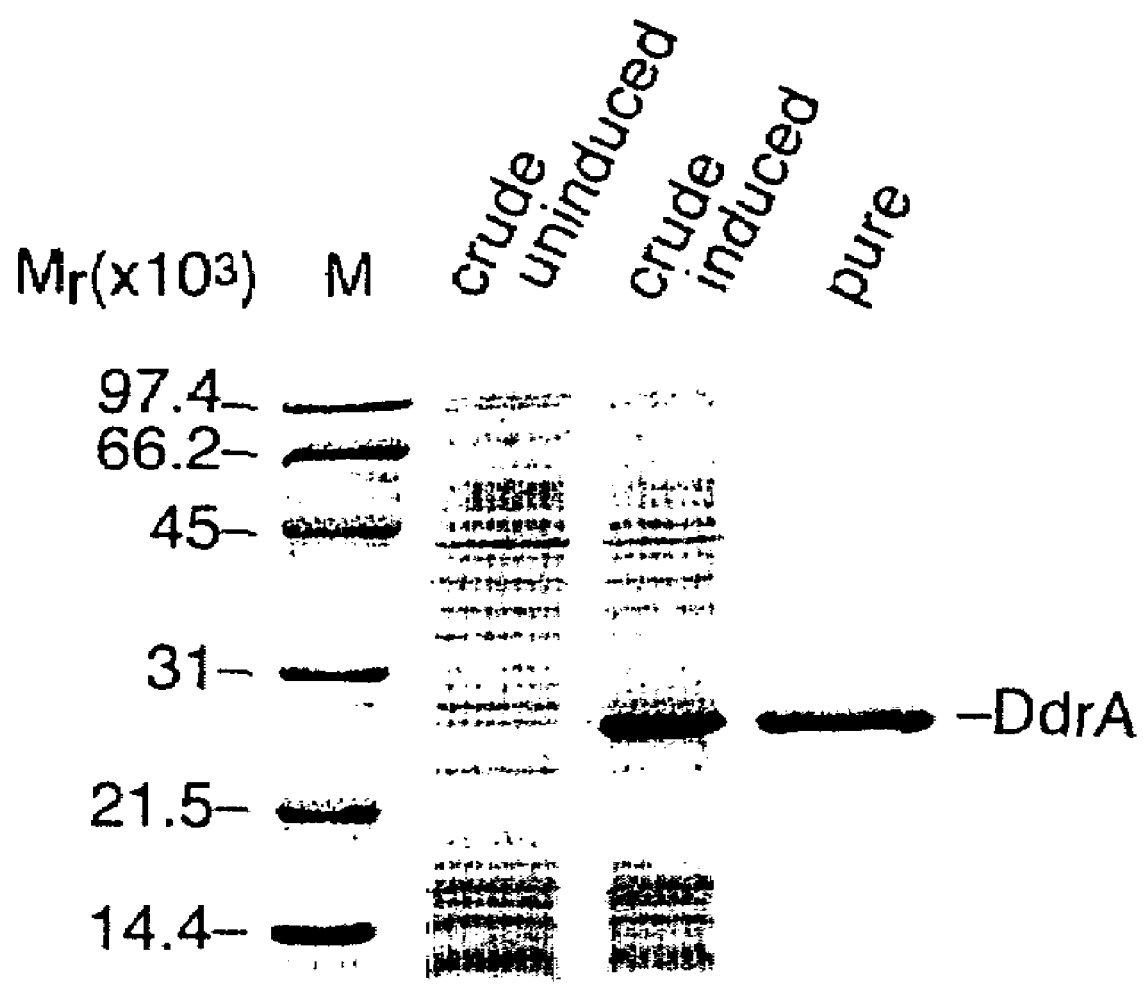
FIG. 6 illustrates purification of the DR0423 (DdrA) protein. The first lane contains molecular weight markers. The second and third lanes contain crude extracts from *E. coli* strain pEAW298 (DdrA overproducer) in which the ddrA gene is uninduced or induced, respectively. The final lane contains purified DdrA protein.

The Purified DdrA Protein Binds the 3' Ends of Single-stranded DNA and Protects Them from Digestion by an Exonuclease The ddrA gene was cloned and expressed in *E. coli*, and the protein was purified to homogeneity (FIG. 6). The identity of the purified protein was confirmed by N-terminal sequencing and mass spectrometry. The deduced N-terminal sequence was MKLSDV, matching the predicted sequence of the first 6 amino acids perfectly (with the initiating methionine retained). The measured mass of the protein was 23012.8+/−3.46 Da, in good agreement with the 23,003.38 Da predicted. In two gel filtration experiments using a Sephacryl S300 column calibrated with molecular weight standards, DdrA eluted as a sharp peak with an apparent mass in the two different trials of 218 and 190 kDa (data not shown). These results suggest that DdrA is an oligomer in solution with 8–10 subunits. Whereas these results are preliminary, Rad52 protein and other members of this family function as large oligomeric rings (Passy, et al., supra, 1999; Iyer, et al., supra, 2002; Singleton, et al., *Proc. Natl. Acad. Sci. USA* 99(21):13492–13497, 2002)

Figure 7:
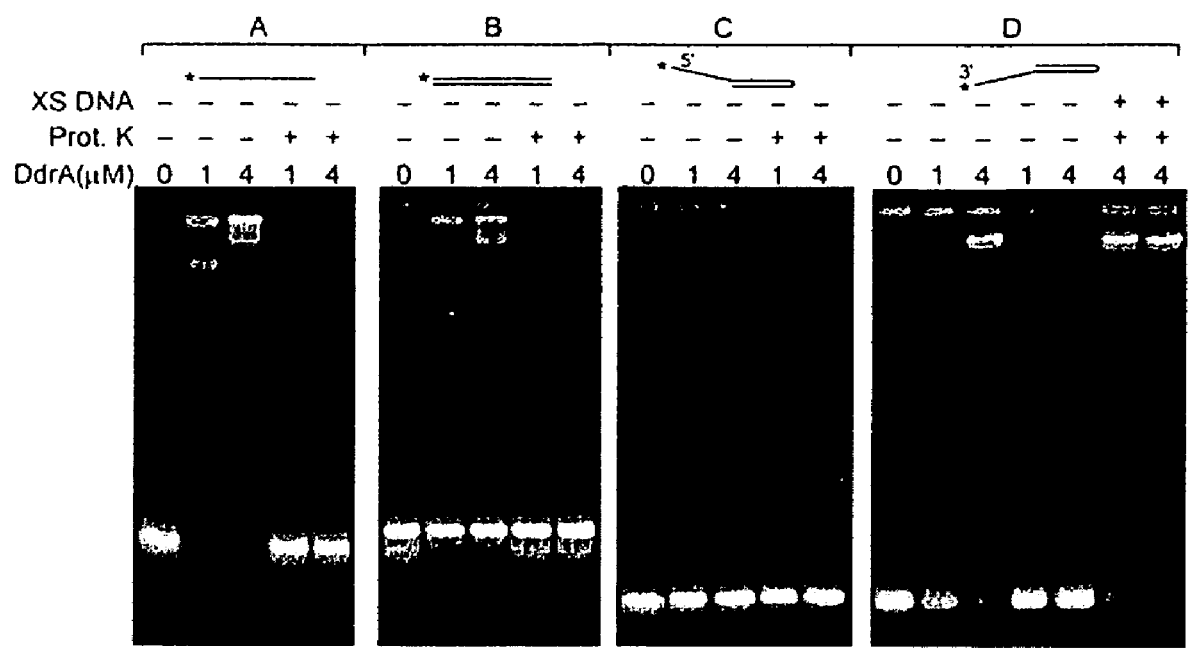
FIG. 7 illustrates DdrA protein binds to single-stranded DNA with free 3' ends. Four sets of EMSA assays are presented, with the gels and electrophoresis conditions carefully matched. DNA substrate concentrations are 0.7 nM in each case, reported as total molecules. In each set, the first three lanes have show the effects of the indicated concentration of DdrA protein. The fourth and fifth lanes are identical to the second and third lanes, respectively, except that they are treated with proteinase K to demonstrate that the DNA has not been altered. In set D, the sixth and seventh lanes are identical to the third lane (with 4 μM DdrA protein), except that they have been challenged with a 1000-fold or 2000-fold excess of unlabeled oligo with a 5' extension, respectively. The unlabeled challenge oligo is the same as that used in reaction set C.

DdrA exhibited no ATPase, helicase, recombinase, or nuclease activity (data not shown). However, it bound to single-stranded DNA as determined by an electrophoretic mobility shift assay (EMSA) (FIG. 7). Binding to duplex DNA depended on the presence of a 3' single-strand extension at one end (FIG. 7), indicating that the protein has some affinity for a free 3' end in single-stranded DNA. This binding was not disrupted by a challenge with a 1000–2000 fold excess of a duplex oligonucleotides with a 5' single-strand extension (FIG. 7).

Figure 8:
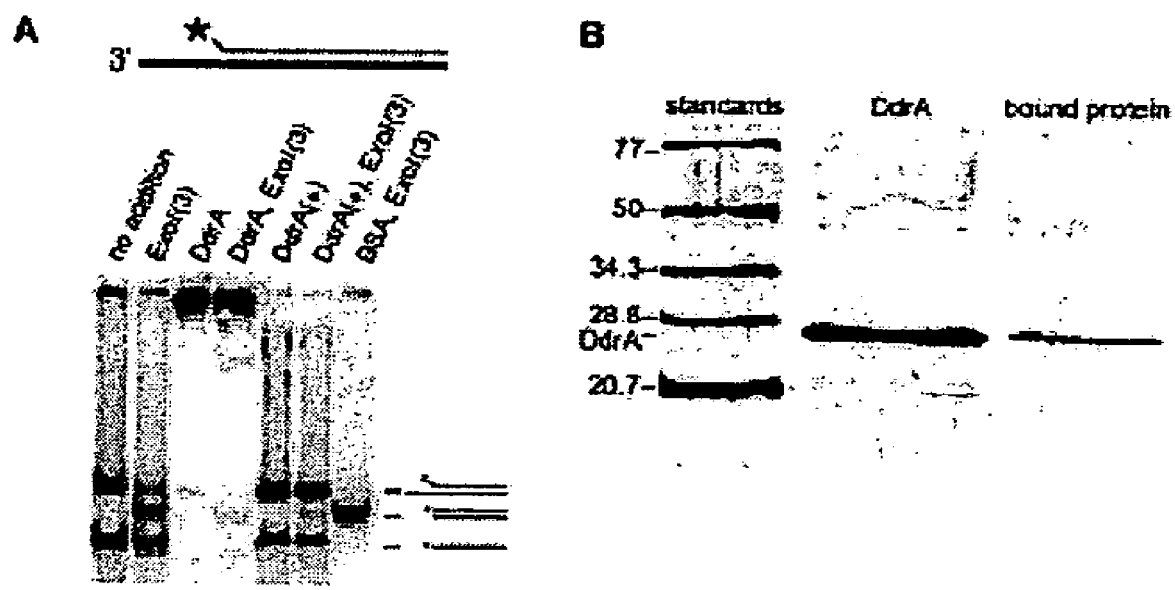
FIG. 8 illustrates DdrA protein protects 3' ends from degradation by exonuclease I.

DdrA also protected the single-stranded DNA from degradation by exonuclease I from *E. coli*, which digests single-stranded DNA from the 3' end (FIG. 8). The DNA binding trials shown in FIG. 8A were scaled up and the bound species was cut out of a preparative gel. The extracted protein co-migrated with DdrA protein on an SDS-polyacrylamide gel (FIG. 8B), providing further confidence that the binding is due to DdrA and not a minor contaminant in the DdrA protein preparation. These results suggest that *D. radiodurans* possesses a novel DNA end-protection system, and that DdrA is a component of that system.

The eukaryotic Rad52 protein has a single-strand annealing activity that may be important to its in vivo function (Mortensen, et al., *Proc. Natl. Acad. Sci. USA* 93:10729–10734, 1996; Sugiyama, et al., *Proc. Natl. Acad. Sci. USA* 95(11):6049–6054, 1998). We carried out several tests to determine if the DdrA protein had a similar annealing activity. In multiple trials using oligonucleotides 30 and 51 nucleotides in length, no DNA strand annealing activity was detected over a range of DdrA concentrations and conditions (data not shown).

Discussion

The extraordinary resistance of *Deinococcus radiodurans* to DNA damage arose not as an adaptation to high levels of radiation, but rather as a response to desiccation (Mattimore and Battista, supra, 1996). In an arid environment, dormant *D. radiodurans* cells would gradually accumulate DNA lesions of all kinds, including strand breaks. Since DNA repair is highly reliant on metabolic energy and appropriate nutrients cannot be assured upon rehydration, it is not unreasonable to expect that this species possesses a means to efficiently repair accumulated damage that minimizes energy use. In this context, mechanisms must have evolved to maintain the genome and protect it from unnecessary degradation by nucleases and other agents. In this study we have identified functions associated with a "hypothetical" protein encoded by *D. radiodurans* R1 that contributes to this species' capacity to tolerate exposure to ionizing radiation and mitomycin C. We propose that the DR0423 protein, which we have designated DdrA, is part of a DNA end-protection system. Induced in response to the appearance of strand breaks generated by ionizing radiation (or subsequent to desiccation), DdrA would cap the strand breaks and help stabilize the genome until such time as conditions were more amenable to systematic DNA repair.

Figure 5:
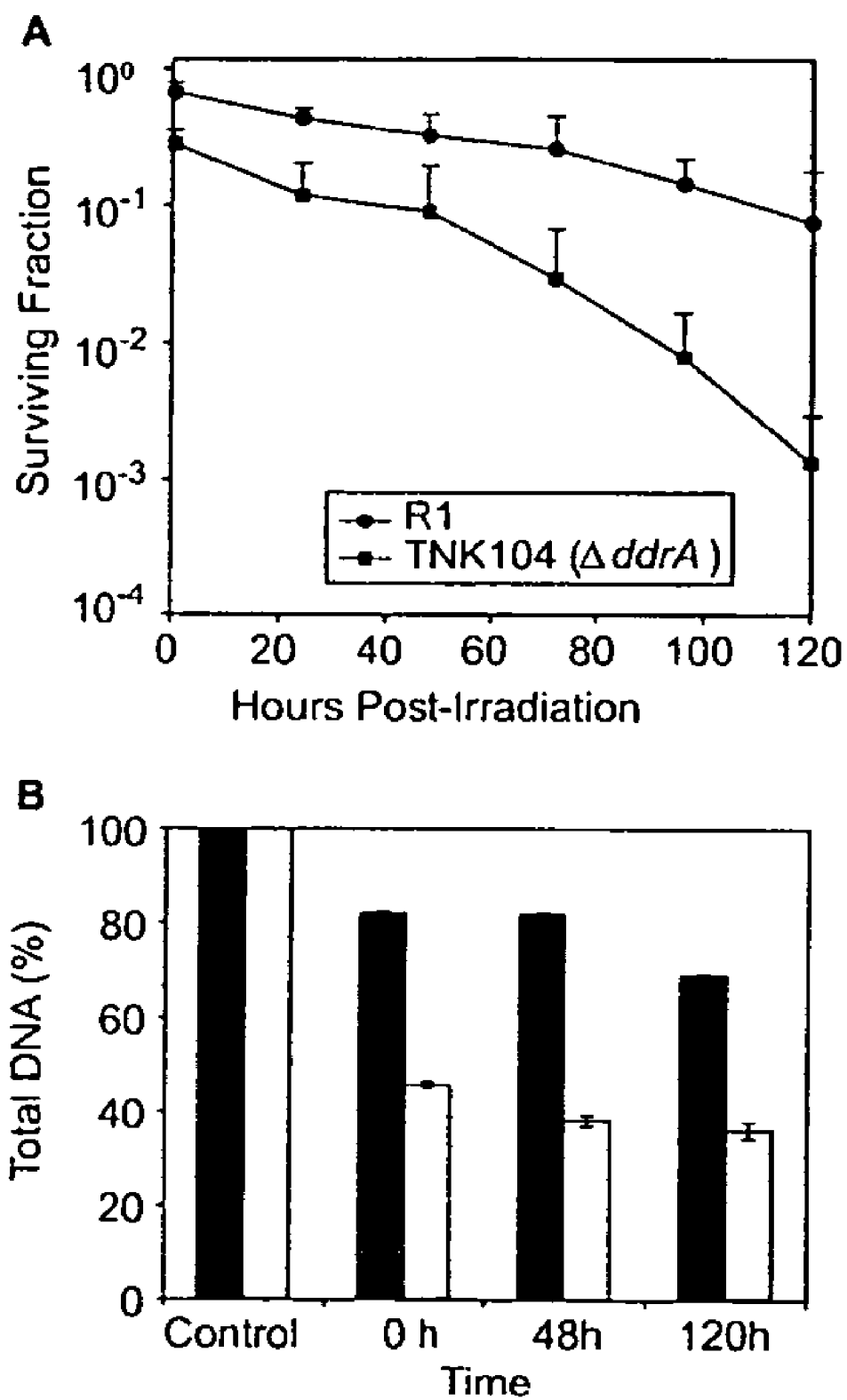
FIG. 5 graphs DdrA protein effects on in vivo survival and genome preservation following exposure to ionizing radiation in the absence of nutrients.

The results we have obtained both in vivo and in vitro are consistent with this hypothesis. When the ddrA (DR0423) gene is deleted from R1, an otherwise wild type cell becomes more sensitive to DNA damaging agents (FIG. 2). We show that DdrA has at least two activities: DdrA contributes to genome restitution following irradiation (FIG. 4), and purified DdrA binds the 3' ends of single-stranded DNA and protects those ends from digestion by exonucleases (FIGS. 7 and 8). Notably, the effects of a ddrA deletion are amplified if nutrients are not provided after exposure to ionizing radiation, and cells held this way for five days display a 100-fold reduction in viability relative to the wild type cells (FIG. 5). In these nutrient-poor conditions, cells lacking DdrA protein do not restore their chromosomes. Instead, the chromosomes are degraded extensively.

Even though the R1 strain was able restore its genome following irradiation and incubation in 10 mM $MgSO_4$, there was no evidence of genome re-assembly in similarly treated cultures of TNK104, the ΔddrA derivative of R1 (FIG. 4). This result indicates that DdrA plays a qualified role in genome restitution. Clearly the protein is necessary for this process in cells held in $MgSO_4$, and we suggest that TNK104's inability to reconstitute its genome under these conditions is likely to be related to the extreme genomic degradation that is observed in this strain following irradiation (FIG. 5B).

DdrA is not needed if cells are allowed to recover in a nutrient-rich medium (FIG. 2). This suggests that the function that DdrA mediates in genome restitution is either redundant or unnecessary when other repair processes are robust. If there is a protein with a redundant activity, it is evident only in rich media. We do not know the identity of the redundant component, or understand why it is not functional in $MgSO_4$. Since DdrA binds the 3' ends of single-stranded DNA, we presume that this protein either has the same activity or is rendered unnecessary by a compensating activity possible only in a nutrient-rich environment (such as DNA synthesis to counter exonucleolytic degradation). If instead, DdrA is part of a passive DNA protection system, this system may be critical under conditions in which active (energy-requiring) DNA repair is not possible, such as when cells are desiccated or held in a nutrient-free media. DdrA may not be as important in a nutrient-rich environment, where active DNA synthesis and other DNA repair processes may compensate for the loss of DNA end-protection.

The increased sensitivity observed in TNK110 (ΔrecA ΔddrA) relative to TNK106 (ΔrecA) indicates that DdrA participates in a process that complements RecA-mediated survival mechanisms (FIG. 3), rescuing some irradiated cells even in the absence of RecA function. Since DdrA is distantly but specifically related to the Rad52 family of eukaryotic proteins, as well as a family of phage-associated proteins that mediate single strand annealing (Iyer, et al., supra, 2002), we speculate that DdrA could be a component of a single strand annealing system that functions simultaneously with RecA-dependent homologous recombination. This possibility is consistent with an earlier report by Daly and Minton (Daly and Minton, *J. Bacteriol.* 178(15):4461–4471, 1996) who documented RecA-independent genome restitution post-irradiation. They reported that approximately 30% of the R1 genome is assembled in a recA background during the first 1.5 hours after exposure, and suggested that this process was single strand annealing. The DdrA protein could act directly or indirectly in any single-strand annealing process that might occur in *Deinococcus*. Although the related Rad52 protein possesses a single-strand annealing activity (Mortensen, et al., supra, 1996; Sugiyama, et al., supra, 1998), we have thus far failed to detect such an activity with DdrA protein. One of three explanations seems likely: i) we have not yet identified suitable conditions for the assay of DdrA-dependent DNA strand annealing, ii) DdrA is part of a complex and other proteins are needed to observe activity, or iii) DdrA does not possess such an activity.

DdrA's capacity to protect the 3' ends of single-stranded DNA from digestion should help maintain the integrity of DNA fragments generated following DNA damage whether those fragments are a result of the direct action of the damaging agent or arise as a consequence of a repair process that cleaves the phosphodiester backbone. By limiting degradation, proteins that protect DNA ends should enhance DNA damage tolerance and cell survival; the stabilized fragments serving as a long-lived substrate for homologous recombination or single-strand annealing. In other words, we suspect that the ability to preserve genetic information is one key to understanding DdrA function and in a larger context the DNA damage tolerance of this species. DNA binding proteins, like DdrA, may be particularly important for surviving desiccation. Like ionizing radiation, the process of desiccation is inherently DNA damaging, introducing large numbers of DNA double strand breaks. Following an extended period of desiccation, broken DNA ends would presumably need to be protected to minimize loss of genetic information. We know of no precedent for an activity of this sort in bacteria, although its existence has been predicted at least once (Clark, *Biochimie* 73(4):523–532, 1991). Bacteriophage are known to encode proteins (e.g., the gene 2 protein of T4 (Wang, et al., *J. Bacteriol.* 182(3):672–679, 2000)) that prevent exonucleolytic digestion of their genomes during infection, and, given its sequence similarity to other phage proteins, it is possible that *D. radiodurans* acquired DdrA from a phage during its evolution.

Since inactivation of DdrA reduces but does not eliminate the DNA damage resistance of *Deinococcus*, we suggest that other proteins with complementary functions, possibly designed to bind DNA ends with different structures, are also encoded by this species, and that the protection provided by these proteins contributes significantly to DNA damage tolerance. By itself, DdrA protein does not enhance the radiation resistance of *Escherichia coli* strains in which it has been expressed (L. Alice Simmons and J. Battista, unpublished data).

It seems likely that *Deinococcus radiodurans*, and other bacteria with similar capacities to survive high DNA damage loads, employs multiple systems to repair their DNA. The DNA end-protection system we have begun to explore may be supplemented by special genome architectures (Levin-Zaidman, et al., *Science* 299(5604):254–256, 2003), traditional DNA repair systems (some with unusual properties (Kim and Cox, *Proc. Natl. Acad. Sci. USA* 99(12):7917–7921, 2002), and perhaps novel enzymatic systems not previously examined. Although we have detected no apparent enzymatic activities in DdrA to augment its DNA binding function, further work is needed to determine if DdrA contributes to single strand annealing or other potential DNA repair pathways. Bound to 3' DNA ends, DdrA would be at a focus of DNA repair activity once genome restitution was initiated. The evolutionary relationship of DdrA to Rad52 may also telegraph a facilitating role in other DNA repair processes.

Materials and Methods

Strains, Growth Conditions, and Treatment

Strains and plasmids used in this study are described in Table 2. All genes are identified as described in the published genome sequence available on the world wide web courtesy of TIGR CMR. All strains derived from *D. radiodurans* were grown at 30° C. in TGY broth (0.5% tryptone, 0.3% yeast extract, 0.1% glucose) or on TGY agar (1.5% agar). *E. coli* strains were grown in Luria-Bertani (LB) broth or on LB plates at 37° C. Plasmids were routinely propagated in *E. coli* strain DH5αMCR. *D. radiodurans* cultures were evaluated for their ability to survive exposure to DNA damaging agents in exponential growth (OD600=0.08–0.15, $5 \times 10^6$ – $1 \times 10^7$ cfu/ml). All cultures were treated at 25° C. Gamma irradiation was conducted using a Model 484R 60Co irradiator (J. L. Shepherd & Associates, San Fernando, Calif.) at a rate of 30 Gy/min. Resistance to mitomycin C was determined by adding one microgram of mitomycin C (Sigma, St. Louis, Mo.) to one ml broth cultures of the *D. radiodurans* strain. Aliquots of the treated culture were removed at one half hour intervals over the next two hours, washed in 10 mM MgSO$_4$, and plated on TGY agar to determine viability.

Construction of TNK104, TNK106, and TNK110

The genes DR0423 and DR2340 (recA) were disrupted by targeted mutagenesis using techniques described previously (Funayama, et al., *Mutat. Res.* 435(2):151–161, 1999). A deletion cassette was created for each locus and transformed into an exponential phase *D. radiodurans* R1 culture. Recombinants were selected on TGY plates containing an appropriate antibiotic. Since *D. radiodurans* is multi-genomic, individual colonies were screened to determine if they were homozygous for the disruption by isolating genomic DNA from putative recombinants and using a PCR-based analysis to determine whether the gene of interest had been deleted. Details for how each strain was generated are given below.

The construction of TNK104 began with the creation of a drug cassette capable of conferring hygromycin resistance on *D. radiodurans*. The hygromycin b phosphotransferase gene (hyg) from pHP45omega-hyg (Blondelet-Rouault, et al., *Gene* 190(2):315–317, 1997) was spliced to the 120 bp of sequence immediately upstream of the initiation codon of the *D. radiodurans* kaA gene (DR1998) (Funayama, et al., supra, 1999) using primers whose sequences overlapped. Subsequently, the katA-hyg fusion product was joined to PCR fragments (Horton, et al., *Gene* 77(1):61–68, 1989) derived from the sequence 1.0 kbp immediately upstream and 0.9 kbp immediately downstream of DR0423. This hybrid fragment was cloned into PGEM-T (Promega, Madison, Wis.), creating pTNK205. pTNK205 was propagated *E. coli* DH5α-MCR. The deletion of DR0423 was accomplished by transforming (Earl, et al., *J. Bacteriol.* 184(4): 1003–1009, 2002b) an exponential phase R1 culture with linear pTNK205. Hygromycin resistant (Hyg$^R$) recombinants were selected on TGY plates containing 37.5 μg/ml hygromycin.

To confirm gene replacement, primers, which anneal outside the coding sequence of DR0423, were used to generate PCR fragments from genomic DNA from Hyg$^R$-colonies and R1. The purified PCR products were restricted with EcoRI and EcoRV. The hyg gene contains an EcoRI site, but DR0423 does not. DR0423 contains an EcoRV site, but hyg does not. In the recombinant, designated TNK104, a single 1.3 kbp fragment, corresponding to the katA-hyg cassette was amplified, whereas there was no trace of the 0.85 kbp fragment, indicative of DR0423 amplification (FIG. 1A). EcoRI cleaved the product amplified from TNK104 into 0.2 kbp and 1.1 kbp fragments, while the R1-derived product remained intact (FIG. 1B). EcoRV digested the amplicon from R1 into fragments of 0.4 kbp and 0.45 kbp, but did not affect the TNK104-derived product (FIG. 1C). We conclude that TNK104 carries a deletion of the DR0423 coding sequence marked by the katA-hyg cassette and that the strain is homozygous for the deletion.

The recA deletion strain TNK106 was constructed in a manner similar to that of TNK104. Initially, the katA promoter of *D. radiodurans* was fused to the chloramphenicol acetyltransferase gene (cat) from pBC (Stratagene Cloning Systems, La Jolla, Calif.). This drug cassette was then spliced to PCR products corresponding to genomic DNA sequence 1.6 kbp upstream and 1.2 kbp downstream of recA by overlap extension, before being cloned into pGEM-T. The resulting plasmid was designated pTNK210. An exponential phase R1 culture was transformed with the replacement cassette from pTNK210 and chloramphenicol resistant (Cm$^R$) recombinants selected on TGY plates containing 3 μg/ml chloramphenicol. Genomic DNA of each recombinant was amplified to determine if the recA coding region was deleted. Purified PCR products amplified using primers that anneal to sequences flanking recA were treated with PvuII and BglII. The cat carries PvuII site, but recA does not. recA contains BglII site, but cat does not. A 1.3 kbp fragment, corresponding to katA-cat cassette, was obtained from a recombinant designated TNK106, but DNA from this recombinant did not generate the 1.5 kbp fragment corresponding to recA (FIG. 1A). Amplifications of genomic DNA from R1 only produced the 1.5 kbp fragments (FIG. 1A). The 1.3 kbp PCR product from TNK106 was cleaved by PvuII to 0.5 kbp and 0.8 kbp fragments, whereas the 1.5 kbp from R1 remained intact (FIG. 1C). BglII cut the R1-derived 1.5 kbp to fragments of 0.45 kbp and 1.05 kbp, but not the product from TNK106 (FIG. 1C). We conclude that recA has been replaced by katA-cat in TNK106 and that the strain is homozygous for this allele. TNK110 is a double mutant in which recA and DR0423 are deleted. This strain was constructed by deleting recA from TNK104 using the protocol described for the creation of TNK106. The construct was verified by the scheme used to identify DR0423 deletion in TNK104 and recA deletion in TNK106 (FIGS. 1A and 1C).

Pulsed-Field Gel Electrophoresis (PFGE). After irradiation at 5.0 kGy cells were collected by centrifugation (6000×g, 15 minutes, 4° C.) and re-suspended in either TGY broth or 10 mM MgSO$_4$ solution, before being placed in a shaking incubator at 30° C. for 24 hours. Aliquots of these cultures were removed at various time points, and cells were washed in 0.9% NaCl and suspended in 0.125 M EDTA pH 8.0 at a density of 5×10$^8$ cells/ml. The suspensions were mixed with low melting-point agarose (Sigma, St Louis, Mo.) to obtain a final concentration of 0.8% agarose. Agarose blocks containing the cell suspension were incubated overnight at 37° C. in 0.05 M EDTA pH 7.5 containing 1 mg/ml of lysozyme. After lysozyme treatment, agarose plugs were placed in ESP buffer (EDTA 0.5 M pH 9–9.5, 1% lauroyl sarcosine, 1 mg/ml proteinase K) at 50° C. for 6 hours, followed by a two day incubation at 37° C. Prior to digestion with restriction enzymes, agarose plugs were washed once with TE buffer pH 7.5 containing 1 mM phenylmethylsulfonyl fluoride (PMSF) and then four times with TE buffer pH 7.5. DNA contained within the agarose plugs was digested with 10 units of NotI restriction enzyme (New England Biolabs, Beverley, Mass.) overnight at 37° C. Restriction digests were analyzed on 1% agarose gels in 0.5×TBE, using a CHEF-MAPPER electrophoresis system (Bio-Rad, Hercules, Calif.) at 6 V/cm for 22 hours at 12° C., with a linear pulse ramp of 10–60 s with a switching angle of 120°. Gels were stained with water containing 0.5 mg/ml ethidium bromide for 20 minutes and destained for 10 minutes in water.

Quantitative Real-time PCR

The protocol followed was the same as that described previously (Earl, et al., supra, 2002a). Total RNA was extracted from one liter cultures of irradiated and non-irradiated exponential phase *D. radiodurans* cultures using TRI Reagent™, (Molecular Research Center, Cincinnati, Ohio) following manufacturer's instructions. Cell disruption was accomplished by adding 100 µl of 0.1 mm zirconia/silica beads (Biospec Products, Bartlesville, Okla.) and TRI Reagent to the cell paste from one liter of cells and vigorously agitating this mixture for 6 minutes with a vortex mixer. Two micrograms of each DNase 1-treated, purified RNA sample were converted to cDNA using SUPER-SCRIPT II™ RNase H⁻ Reverse Transcriptase (Invitrogen, Carlsbad, Calif.) combined with 25 pmol of random hexamers to initiate synthesis. Conditions for this reaction followed the manufacturer's instructions.

Approximately 100 bp of unique sequence from the genes encoding DR0423, RecA (DR2340) and glyceraldehyde 3-phosphate dehydrogenase (DR1343) were amplified using the following primer sets: DR0423up
(5'GGTGCAGGACCGACTCGACGCCGTTTGCC3', SEQ ID NO:4), DR0423down
(5'CCTCGCGGGTCACGCCGAGCACGGTCAGG3', SEQ ID NO: 5), DR2340up
(5'GTCAGCACCGGCAGCCTCAGCCTTGACCTC3', SEQ ID NO:6), DR2340dwn
(5'GATGGCGAGGGCCAGGGTGGTCTTGC3', SEQ ID NO:7), and DR1343up
(5'CTTCACCAGCCGCGAAGGGGCCTCCAAGC3, SEQ ID NO:8), DR1343dwn (5'GCCCAGCACGATGGAGAAGTCCTCGCC3', SEQ ID NO:9). The PCR reaction (50 µl) for amplifying these genes contained the appropriate primers at a final concentration of 0.2 µM, 1 µl of the cDNA template and SYBR Green PCR Core Reagents (Applied Biosystems, Foster City, Calif.). Amplifications were carried out by incubating reactions at 95° C. for 3 minutes prior to 40 cycles of 30 seconds at 95° C. followed by 30 seconds at 65° C. and 72° C. for 30 seconds. Data was collected and analyzed at each 72° C. interval. Each 96-well plate consisted of standard curves for each primer set run in duplicate. Standard curves were constructed using cDNA obtained from the un-irradiated wild type organism. A dilution series ($1-1\times10^{-4}$) of each experimental sample was generated and run in duplicate. Negative controls without cDNA template were run on every plate analyzed. All assays were performed using the iCycler iQ™ Real-Time Detection System (Bio-Rad, Hercules, Calif.). All data was PCR baseline subtracted before threshold cycle values were designated and standard curves were constructed. Mean concentrations of the transcripts in each sample were calculated from the standard curves generated using the DR2340 primer set. Induction levels were determined by dividing the calculated concentration of transcript from the irradiated sample by the concentration of transcript from the unirradiated sample for each strain. The mean concentration of the glyceraldehyde 3-phosphate dehydrogenase (gap) transcript, a housekeeping gene whose expression is unaffected by ionizing radiation, was also determined before and after irradiation for each strain.

DNA Content Measurement in TNK 104 and R1 Cells

Overnight cultures growing in TGY media were harvested at room temperature. Control cultures aliquots were fixed with 1% toluene (final vol/vol), shaken vigorously and stored at 4° C. The fixed bacteria were diluted (¹/₁₀, ¹/₁₀₀ and ¹/₁₀₀₀) in 3 ml (final volume) of dilution buffer: 10 mM NaCl, 6.6 mM $Na_2SO_4$, 5 mM N'-2-hydroxyethylpiperazine-N'-2-ethanesulfonic acid (HEPES; pH 7.0). The remaining cultures were centrifuged for 20 minutes at 4° C. at 7,000 rpm. Bacterial pellets were washed twice and resuspended in 10 mM.

$MgSO_4$ for gamma irradiation. Cell suspensions were irradiated at 5,000 Gy and incubated at 30° C. for 120 hours. Aliquots were removed immediately following irradiation, at 48 and at 120 hours post-irradiation. Cells were toluene-fixed as previously described above. 100 ml of DAPI (stock solution at 3 mg/ml) was added to each dilution tube and mixed. The fluorescence intensity was measured with excitation at 350 nm and emission at 450 nm.b Cloning, Overexpression, and Purification of DR0423 (DdrA)

DR0423 gene was amplified using the genomic DNA from *Deinococcus radiodurans* strain R1. PCR primers were designed according to the DR0423 gene sequence annotated in the genomic bank available on the world wide web courtesy of NCBI. The gene was cloned in *E. coli* overexpressing plasmid pEA W298. DR0423 overproducing cells were lysed with lysozyme and the protein was precipitated from the supernatant by adding ammonium sulfate to 30% saturation. The protein was purified with DEAE and hydroxyapatite chromatography to >99% purity. The identity of the purified protein was confirmed by N-terminal sequencing (Protein and Nucleic Acid Chemistry Laboratory, Washington University School of Medicine, St. Louis, Mo.) and accurate mass determination (Biotech Center, University of Wisconsin, Madison, Wis.). The protein was transferred into the storage buffer (20 mM Tris-Acetate, 80% cation, pH 7.5/50% (w/v) glycerol/0.5M NaCl/0.1 mM EDTA/1 mM DTT) and stored at −80° C.

Determination of the Extinction Coefficient for Pure DR0423 (DdrA) Protein.

The extinction coefficient for DdrA protein protein was determined using a modification of a published procedure (6). UV absorbance spectra were measured by using a Cary 300 dual-beam spectrophotometer (Varian). The temperature was maintained using a circulating water bath. Cell path length and bandwidth were 1 cm and 0.5 nm, respectively. The extinction coefficient for native DdrA protein was determined in the storage buffer, by comparing the absorbance spectra of the native protein to the absorbance spectra of the protein denatured in 6 M guanidine hydrochloride (Gnd-HCl) in storage buffer. The extinction coefficients at 280 nm of glycyl-L-tyrosylglycine and N-acetyl-L-tryptophanamide in 6 M Gnd-HCl are 1280 $M^{-1}cm^{-1}$ and 5690 $M^{-1}cm^{-1}$, respectively (7). In the DdrA protein there are 5 tyrosine, 5 tryptophan and 2 cysteine residues in a protein with a total molecular mass of 23 kDa. Even if all cysteine residues were involved in disulfide bonds, the contribution of cystine to the absorbance of DdrA protein is predicted to be less than 1% and was neglected from our calculations. The extinction coefficient at 280 nm for denatured DdrA protein in 6 M Gnd-HCl was calculated as $\epsilon_{denat,\ 280\ nm}=5\times 5690+5\times 1280=3.485\times 10^4\ M^{-1}cm^{-1}$. Absorbance spectra of native and denatured (6 M Gnd-HCl) DdrA protein were scanned at 25° C., from 320 to 240 nm, for 5 different dilutions and with two different protein preparations. DdrA protein was diluted in storage buffer or storage buffer+6 M Gnd-HCl (final concentration) in a total volume of 80 µl and was pre-incubated at 25° C. for 5 minutes before scanning. Each dilution was carried out in triplicate and the absorbance values at 280 nm were averaged. The concentrations of native and denatured protein were equal to each other in each scan at each dilution. The extinction coefficient of native DdrA protein at 280 nm was determined according to the expression (8): $\epsilon_{nat,\ 280\ nm}=\epsilon_{denat,\ 280\ nm}\times Abs_{nat,\ 280\ nm}/Abs_{denat,\ 280\ nm}$. We used 5 determinations with two different protein preparations, yielding an average extinction coefficient of $\epsilon_{nat,\ 280\ nm}=2.8728+/-0.1999\times10^4$ $M^{-1}\ cm^{-1}$ in storage buffer at 25° C. The $A_{280}/A_{260}$ ratio for the native DdrA protein is 1.575+/−0.00091. The error in both cases is one standard deviation.

DNA Binding Assay

The duplex oligonucleotide with a 3' single strand extension was hairpin-forming oligonucleotide A (5' TTA ACG ACC GTC GAC CTG CAG GTC GAC GGT CGT TAA CGT CTC TCA GAT TGT 3', SEQ ID NO:10), which was labeled at the 3'terminus with [α-$^{32}$P]ddATP, using terminal transferase. After labeling, hairpin formation generated an 18 bp duplex hairpin with a 16 nucleotide 3' extension. The duplex oligonucleotide with a 5' single strand extension was hairpin-forming oligonucleotide B (5' CGT CTC TCA GAT TGT TTA ACG ACC GTC GAC CTG CAG CTG CAG GTC GGT TAA 3', SEQ ID NO:11). The oligo was labelled at the 5' end using [γ-$^{32}$P] and polynucleotide kinase. After labelling, hairpin formation generated a DNA with 18 bp in the hairpin duplex and a 15 nt 5' extension. A blunt-ended duplex DNA fragment was prepared by annealing oligonucleotide C (5' GGT CTT TCA AAT TGT TTA AGG AAG AAA CTA ATG CTA GCC ACG GTC CGA GCC 3', SEQ ID NO:12) $^{32}$P-labeled at its 5' end, with unlabeled oligonucleotide D (5' GGC TCG GAC CGT GGC TAG CAT TAG TTT CTT CCT TAA ACA ATT TGA AAG ACC 3', SEQ ID NO:13). The single-stranded oligonucleotide was the end-labeled oligo C. Electrophoretic mobility shift assays (EMSA) for DNA binding were carried out in 15 μl reaction mixtures containing the reaction buffer (40 mM Tris-Acetate, pH 7.5, 10% glycerol (w/v), 0.1 M NaCl, 0.1 mM EDTA, 1 mM DTT) and 0.7 nM (60 nM nt) $^{32}$ P-labeled duplex.

DNA. The reaction was initiated by adding the DR0423 (DdrA) protein to the required concentration. The reaction mixture was incubated at 30° C. for 30 minutes and loaded onto 10% native polyacrylimide gel. The electrophoresis was performed in 1×TBE (89 mM Tris-Borate (pH 8.3), 2 mM EDTA) at room temperature. After the electrophoresis was complete the gel was dried and exposed with phospho-imager.

Identification of DdrA Protein in DNA-protein Complex

The general strategy of this experiment was to incubate a DNA duplex with a 3' extension with DdrA protein, resolve the protein-complex in native PAGE, excise the complex from the gel, extract the protein from the slice and analyze the protein in SDS-PAGE. If the protein is DdrA it will co-migrate with DdrA protein in SDS-PAGE.

A $^{32}$P-labeled oligonucleotide (30 nt; 5'-GTG CGC TCC GAG CTC AGC TAC CGC GAG GCC-3', SEQ ID NO:14) was annealed with a longer unlabeled oligonucleotide (50 nt; 5'-GGC CTC GCG GTA GCT GAG CTC GGA GCG CAC GAT TCG CAC TGC TGA TGT TC -3', SEQ ID NO:15). Annealing was carried out in a 40 μl solution containing 0.5 μM of each oligonucleotide in 25 mM Tris HCl (pH 8), 50 mM NaCl, and 12.5 mM $MgCl_2$. The solution was heated briefly at 100° C. by transferring the closed tube to a beaker of boiling water, and allowed to cool slowly overnight. The tube was refrigerated for several hours and then stored at −20° C. until use.

The resulting labelled duplex DNA with a 3' extension (0.7 nM) was incubated with 4 μM DdrA protein under the DNA binding conditions described above. The mixture was loaded onto a 10% native polyacrylamide gel. Electrophoresis was performed as described above. The gel was exposed with X-ray film to map the position of the protein-duplex complex. The complex was cut out of the gel. The gel slice was frozen in liquid nitrogen and crushed into a slurry with a plastic stick. The slurry was mixed with an equal volume of SDS-PAGE loading buffer, and boiled for 3 minutes. The mixture was loaded onto a 12% SDS-PAGE gel and the protein present compared to molecular weight standards and purified DdrA protein.

Exonuclease Assay

The duplex with a 3' extension was prepared by annealing oligonucleotide A (5' CTA GCA TTA GTT TCT TCC TTA AAC AAT TTG AAA GAC C 3', SEQ ID NO:16), which was labelled at the 5' terminus with [γ-$^{32}$P]ATP, and cold oligonucleotide B (5' GGT CTT TCA AAT TGT TTA AGG AAG AAA CTA ATG CTA GCC ACG GTC CGA GCC 3', SEQ ID NO:12). The annealing generated a 14 nt 3' extension at one end of the short duplex. Before adding the exonuclease, the $^{32}$P-labeled duplex (60 nM (nucleotides)) was preincubated with the DR0423 (DdrA) protein at the indicated concentration in 15 μl of the exonuclease reaction buffer (40 mM Tris-acetate, pH 7.5, 0.1 M NaCl, 10 mM $MgCl_2$ 0.1 mM EDTA, 1 mM DTT, 10% glycerol) at room temperature for 10 minutes. In the control experiment, the DR0423 protein was replaced with BSA. Exonuclease I was added to 200 U/ml and the reaction mixture was incubated at 37° C. for 30 minutes. After the incubation was complete, the reactions 5–8 and 10 was deproteinized with 0.2% SDS and 0.2 mg/ml proteinase K at 37° C. for 15 minutes. The DNA-protein complexes were resolved in the native polyactylamide gel as above.

TABLE 1

Relative expression of the DR0423, recA, and gap genes of *Deinococcus radiodurans* R1 following exposure to 3000 Gy ionizing radiation. Relative expression was determined before and after irradiation by calculating transcript abundance using Q-RT-PCR. The numbers in this table are the ratio of transcript present post-irradiation to that present pre-irradiation. Values are the means of ratios calculated from three independent experiments (n = 6). The ranges of values obtained are included in parentheses adjacent to each mean. A value greater than 1 indicates an increase in expression in response to ionizing radiation.

| Gene | | Mean Ratio (Range) Time Post-Irradiation (min) | | |
|---|---|---|---|---|
| Designation | Name | 0 | 30 | 60 |
| DR0423 | ddrA | 13 (10–17) | 23 (20–28) | 11 (7–14) |
| DR2340 | recA | 7 (4–10) | 13 (12–15) | 6 (5–7) |
| DR1343 | gap | 1 (0.8–1.1) | 1 (0.4–1.4) | 1 (0.6–1.4) |

TABLE 2

Strains and Plasmids

|  | Description | Reference |
|---|---|---|
| Strains | | |
| *Deinococcus radiodurans* R1 | ATCC13939 | (Anderson, et al., Food Technol. 10: 575–578, 1956) |
| TNK104 | as R1 but ☐DR0423 | this study |
| TNK106 | as R1, but ☐recAl | this study |
| TNK110 | as TNK106, but ☐recA | this study |
| DH5☐-MCR lacZ☐15 ☐lacX74 endA1 recA1 galK nupG rpsL | F mcrA ☐(mrr-hsdRMS-mcrBC) ☐80 Grand Island, NY | Invitrogen, Inc. deoR ☐(ara-leu) 7697 araD139 galU |
| Plasmids | | |
| pHP45omega-hyg | ATCC87627 | (Blondelet-Rouault, et al., Gene 190(2): 315–317, 1997) |
| pGEM-T | | Promega |
| pBC | | Stratagene |
| pTNK205 | | this study |
| pTNK210 | | this study |

Fluorescence Anisotropy Data for DdrA Binding to Single-Stranded DNA

Figure 9:
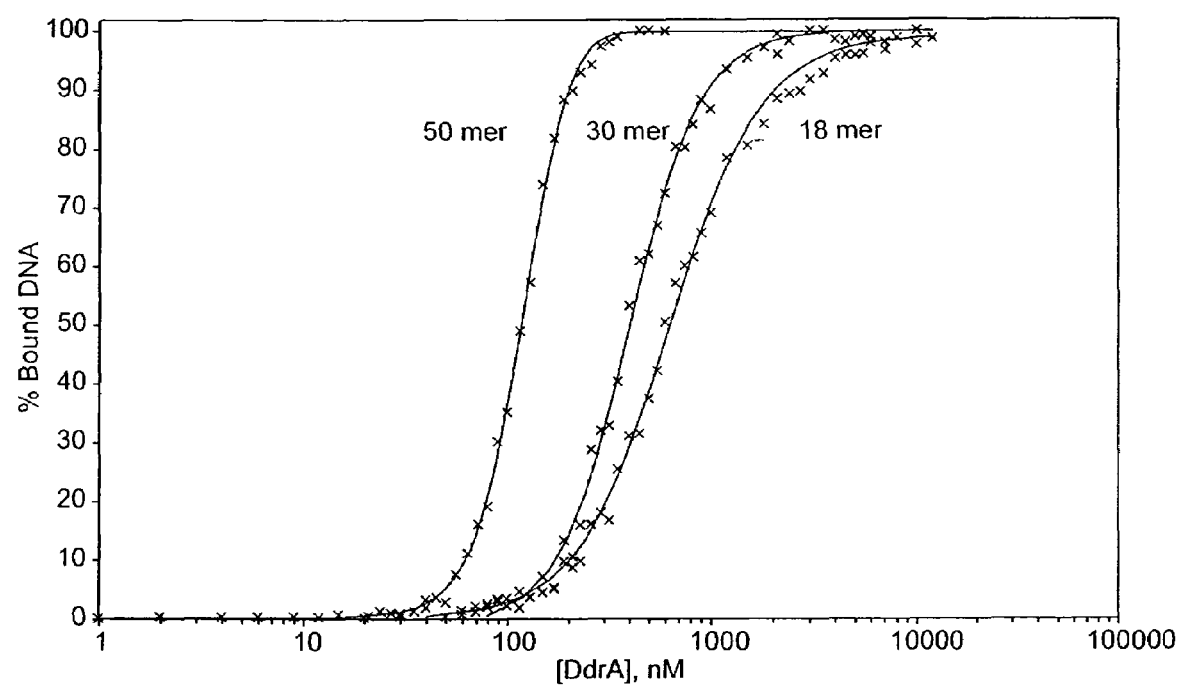
FIG. 9 is a graph of fluorescence anisotropy data for DdrA binding to single-stranded DNA. Increasing concentrations of DdrA protein were incubated with 3'-fluorescently tagged DNA (1.0 nM) at 30° C. for 30 minutes. Samples were analyzed using the Beacons 2000 Fluorescence Polarization System and a curve was generated suing CURVE EXPERT 1.3 software.

FIG. 9 is a graph of fluorescence anisotropy data for DdrA binding to single-stranded DNA. Increasing concentrations of DdrA protein were incubated with 3'-fluorescently tagged DNA (1.0 nM) at 30° C. for 30 minutes. Samples were analyzed using the Beacons 2000 Fluorescence Polarization System and a curve was generated suing CURVE EXPERT 1.3 software. The $K_{D,app}$ for each substrate is the concentration of DdrA when 50% of the DNA is bound as determined by the generated curve fit. The $KD_{,app}$ on 18 nt ssDNA is 640 nM. The $KD_{,app}$ on 30 nt ssDNA is 406 nM. The $K_{D,app}$ on 50 nt ssDNA is 118 nM.

(SEQ ID NO:17)
18nt- 5'-AAG CAC AAT TAC CCA CGC-3'

(SEQ ID NO:18)
30nt- 5'-GCG TGG GTA ATT GTG CTT CAA TGG ACT GAC-3'

(SEQ ID NO:15)
50nt- 5'-GGC CTC GCG GTA GCT GAG CTC GGA GCG CAC GAT TCG CAC TGC TGA TGT TO-3'

---

We claim:

1. A method of protecting a 3' end of a DNA molecule from exonuclease damage comprising the step of exposing the DNA molecule to an amount of a pure preparation of DdrA protein effective to decrease exonuclease damage in relation to natural exonuclease damage that would occur in the absence of DdrA, wherein the DdrA protein consists of SEQ ID NO:2.

2. A method of protecting a 3' end of a DNA molecule from exonuclease damage comprising the step of exposing the DNA molecule to an amount of a PURE preparation of DdrA protein effective to decrease exonuclease damage in relation to natural exonuclease damage that would occur in the absence of DdrA, wherein the DdrA protein consisting of SEQ ID NO:2, and wherein the DdrA protein is incubated with at least a first and a second linear duplex DNA each with a 3'-ending strand and a 5'-ending strand, wherein the first linear duplex DNAs comprises an end that is complementary to an end of the second linear duplex DNA.

3. The method of claim 2 further comprising the step of exposing the first and second DNA molecule to a exonuclease, wherein the DdrA protein protects the 3' ending strands while allowing the 5' ending strands to be degraded, thereby producing single-stranded extensions with 3' ends on both first and second DNAs.

4. The method of claim 3 further comprising the steps of annealing the single stranded extensions of the first and second DNAs, thereby producing a joined first and second DNA.

5. The method of claim 4 further comprising the steps of processing the joined DNA with a nuclease, a DNA polymerase, and a DNA ligase to make the joined DNA contiguous.

6. The method of claim 5, wherein the method is used to join the first and second DNAs of at least 1 Kb each.

7. The method of claim 6, wherein the method reconstructs the first and second DNAs from mixtures of multiple DNA fragments of greater than 1 Kb.

8. The method of claim 1 additionally including the step of exposing the DNA molecule to DrSSB.

9. The method of claim 1 wherein the DNA is between 0.1–100 nanomolar.

10. The method of claim 1 wherein the DdrA protein is between 1 nanomolar–100 micromolar.

11. The method of claim 10 wherein the concentration of DdrA is 1–10 micromolar.

12. The method of claim 1 wherein the DNA is protected for at least 30 minutes.

13. The method of claim 2 additionally including the step of exposing the DNA molecule to DrSSB.

14. The method of claim 5 wherein DNA is between 0.1–100 nanomolar.

15. The method of claim 5 wherein the DdrA protein is between 1 nanomolar–100 micromolar.

* * * * *